US011953397B2

(12) United States Patent
Coleman et al.

(10) Patent No.: US 11,953,397 B2
(45) Date of Patent: Apr. 9, 2024

(54) NANOCOMPOSITE MATERIAL AND USES THEREOF

(71) Applicant: THE PROVOST, FELLOWS, SCHOLARS AND OTHER MEMBERS OF BOARD, OF TRINITY COLLEGE OF DUBLIN, Dublin (IE)

(72) Inventors: Jonathan Coleman, Dublin (IE); Daniel O'Driscoll, Dublin (IE); Conor Boland, Dublin (IE); Sean McMahon, Dublin (IE)

(73) Assignee: THE PROVOST, FELLOWS, SCHOLARS AND OTHER MEMBERS OF BOARD, OF TRINITY COLLEGE OF DUBLIN;, Dublin (IE)

( * ) Notice: Subject to any disclaimer, the term of this patent is extended or adjusted under 35 U.S.C. 154(b) by 30 days.

(21) Appl. No.: 17/175,076

(22) Filed: Feb. 12, 2021

(65) Prior Publication Data
US 2021/0262875 A1 Aug. 26, 2021

(30) Foreign Application Priority Data
Feb. 12, 2020 (EP) .................................... 20156998

(51) Int. Cl.
*G01L 5/00* (2006.01)
*G01L 1/22* (2006.01)
(52) U.S. Cl.
CPC .......... *G01L 5/0095* (2013.01); *G01L 1/2287* (2013.01)

(58) Field of Classification Search
CPC .......................... G01L 5/0095; G01L 1/2287
See application file for complete search history.

(56) References Cited

U.S. PATENT DOCUMENTS

| | | | |
|---|---|---|---|
| 9,868,875 B2 | 1/2018 | Rudhardt et al. | |
| 11,466,169 B2* | 10/2022 | Bodkhe | C09D 11/033 |
| 2003/0099798 A1* | 5/2003 | George | C08L 77/02 |
| | | | 264/141 |
| 2008/0191177 A1 | 8/2008 | Mainwaring et al. | |
| 2010/0063779 A1 | 3/2010 | Shrock et al. | |
| 2014/0011969 A1 | 1/2014 | Panchapakesan | |
| 2016/0033403 A1 | 2/2016 | Packirisamy et al. | |
| 2016/0209281 A1 | 7/2016 | Carrasco Vergara et al. | |
| 2017/0354372 A1* | 12/2017 | Varadan | A61B 5/282 |

(Continued)

FOREIGN PATENT DOCUMENTS

| | | |
|---|---|---|
| CN | 107201089 A | 9/2007 |
| EP | 2562766 A1 | 2/2013 |

(Continued)

OTHER PUBLICATIONS

XP-002799310, WPI Clarivate Analytics, 1-2, (2017).

(Continued)

*Primary Examiner* — Max H Noori
(74) *Attorney, Agent, or Firm* — NIXON PEABODY LLP; David S. Resnick; Ravinderjit Braich

(57) ABSTRACT

An ink blend consisting of a polymer, a weakly cross-linking agent and a nanomaterial deposited to form a thin polymer-nanomaterial composite film with unique mechanical and electrical properties suitable for high performance strain sensing applications.

17 Claims, 11 Drawing Sheets

(56) References Cited

U.S. PATENT DOCUMENTS

| | | | |
|---|---|---|---|
| 2017/0370785 A1 | 12/2017 | Jenn | |
| 2018/0022023 A1* | 1/2018 | Therriault | C09D 7/61 |
| | | | 264/460 |
| 2018/0171160 A1* | 6/2018 | Sarto | C01B 32/19 |
| 2019/0094089 A1 | 3/2019 | Lewis et al. | |
| 2019/0152137 A1* | 5/2019 | Chaffins | H05K 1/095 |
| 2019/0185672 A1* | 6/2019 | Boland | C08K 3/04 |

FOREIGN PATENT DOCUMENTS

| | | | |
|---|---|---|---|
| EP | 3279247 A1 | 7/2018 | |
| WO | 2017114978 A1 | 7/2017 | |
| WO | WO-2017180162 A1 * | 10/2017 | B29C 64/153 |

OTHER PUBLICATIONS

Boland et al., "Sensitive electromechanical sensors using viscoelastic graphene-polymer nanocomposites", Science, 354, (6317), 1257-1260, (2016).

Lee et al., "High strain biocompatible polydimethylsiloxane-based conductive graphene and multiwalled carbon nanotube nanocomposite strain sensors", Applied Physics Letters, 102, (183511), 1-5, (2013).

Boland, "Stumbling Through the Research Wilderness, Standard Methods to Shine Light on Electrically Conductive Nano Composites for Future Healthcare Monitoring," ACS Nano 13(12): 13627-13636 (2019).

Wang et al. "Graphene/polydimethylsiloxane nanocomposite strain sensor." Review of Scientific Instruments 84(10): 105005 (2013).

\* cited by examiner

NANOCOMPOSITE MATERIAL AND USES THEREOF

CROSS-REFERENCE TO RELATED APPLICATIONS

This application claims benefit under 35 U.S.C. § 119(b) of European Patent Application No. EP20156998.5 filed Feb. 12, 2020, at the European Patent Office, the content of which is incorporated herein by reference in its entirety.

FIELD OF THE INVENTION

The invention broadly relates to a polymer-based nanocomposite ink and its use as a polymer-nanomaterial composite film. The invention relates to a printable graphene-putty for use in frequency and rate independent, high performance strain sensors.

BACKGROUND TO THE INVENTION

Strain sensors are often fabricated from piezoresistive materials whose electrical resistance changes as they are deformed. Such sensors are important for a number of applications with particular attention being given to soft, wearable sensors which can monitor vital signs such as pulse and breathing. In recent years, nanocomposite strain sensors, consisting of a conducting nanomaterial in a polymeric matrix, have been heavily studied. Such materials have a number of advantages in that they are easily processed, for example via printing, and, depending on the matrix, can be very soft and so skin mountable. Although their electrical conductivity is generally not high, they can be extremely ductile and have high sensitivity or gauge factor G (defined by the ratio of fractional resistance (R) change and strain ($\varepsilon$): $\Delta R/R_0 = G\varepsilon$). One recently reported nanocomposite sensing material, a graphene-polysilicone mixture called G-putty, displayed extremely high gauge factors of up to 500.

However, nanocomposite strain sensors have a number of significant disadvantages. In particular, when used as sensors, they can introduce resistance hysteresis and render the gauge factor strongly rate-dependent. These are significant problems for strain sensors which require a unique relationship between resistance and strain. A good example of this problem is found with G-putty whose extreme softness results in severe viscoplastic relaxation on straining. This means that even though G-putty has an extremely high gauge factor, it cannot be used to fabricate real strain sensors. Furthermore, there is evidence to show that the high gauge factor displayed by G-putty is intrinsically linked to its low viscosity further complicating matters.

In addition, metal foil strain gauges are considered to be the industry standard for commercial strain sensing technology due to the relative ease and low cost with which they can be manufactured compared to other high-end strain sensors. However, there are a number of limitations with these gauges such as low, fixed and/or strain rate-dependent sensitivity, being uni-directional in their sensing ability, having limited resolution or substrate limitations.

Boland et al. (Science, 354(6317), pp. 1257-1260 (2016)) describes dispersing graphene inside a PDMS matrix crosslinked with boric acid to form a viscoelastic material that allows the dispersed graphene flakes to be mobile at room temperature. This material is then mixed with exfoliated graphene flakes dispersed in chloroform (exfoliated in NMP). Once the solvent has evaporated, the remaining material is the sensing material (G-putty) used in the paper with a gauge factor of ~500. However, a continuous decrease in the electrical resistance of the material is observed when the material is in a static, unloaded position. The material is also strongly rate-dependant, meaning that as the strain rate decreases, it is observed that there is a ~95% decrease in sensitivity over a range of strain rate.

Wang et al. (Review of Scientific Instruments, 84(10), p. 1-5 (2013)) describes the fabrication of graphene/PDMS composites. The authors use a PDMS based pre-polymer oil, a curing agent (together sold as the SYLGARD®-184 elastomer kit) and graphene nano-powder. An additional amount of the tetrahydrofuran (THF) was added to the prepolymer in a 6:1 volume ratio in order to decrease the viscosity of the prepolymer and ensure a better dispersion of the graphene nano-powder into the matrix. However, this material is permanently (covalently) cross-linked which results in a composite that is significantly stiffer and non-elastic than materials which are temporally crosslinked. This has a significant effect on the mechanical, electrical and sensing properties of the material described in Wang.

It is an object of the present invention to overcome at least one of the above-referenced problems.

SUMMARY OF THE INVENTION

The inventors have provided a method to fabricate and process nanocomposite sensing materials with high gauge factor and conductivity but where the hysteresis and rate-dependence have been suppressed. There is described an ink blend comprising a polymer (such as polydimethylsiloxane (PDMS)), a weak crosslinking agent (such as boric acid) that provides temporal (non-permanent) or non-covalent cross links between polymer chains and a nanomaterial (such as graphene) deposited to form a printed polymer-nanomaterial composite film with unique mechanical and electrical properties suitable for high performance strain sensing applications. The polymer used in the examples is polydimethylsiloxane (PDMS)—an inert, non-toxic, non-flammable silicone-based polymer widely used in both commercial and research settings. The weak crosslinking agent in the examples is boric acid, used to form temporary (non-covalent; non-permanent) crosslinks between polymer chains of the PDMS, which influences the formation of the distinct film morphology upon deposition, allowing for superior sensing properties. The nanomaterial used in the examples is graphene—sheets of a carbon atoms a few atoms thick provide with excellent mechanical and electrical properties. The ink described herein can be deposited using a wide variety of printing methods (screen printing, aerosol, and mechanical deposition) resulting, once the ink dries, in the formation of a polymer-nanomaterial composite film. During the drying process, the film takes on a distinct morphology which makes it extremely sensitive to any external stresses. These stresses can be detected by monitoring the electrical resistance of the film. When the film is strained by an external force, an increase in the electrical resistance of the material is registered. The sensitivity of this invention is such that it can detect extremely small external forces, e.g., the forces associated with arterial contraction and expansion due to heart beats, breathing, and microstrains associated with material deformation. The combination of the polymer and nanomaterial result in a composite which has the mechanical robustness necessary to perform large number of sensing cycles without a drop in performance along with the necessary electrical characteristics for integration into a commercial device. The invention displays a sensing ability that is independent of the rate of strain of the device—the material is as sensitive when a stress is applied over a long period of time as when the same stress is applied over a shorter period. This is not the case for several nanocomposite and traditional sensors. This invention has an extremely low-cost associated with manufacturing and is capable of being scaled to an industrial level of production.

According to the invention, as set out in the appended claims, there is provided a printed nanocomposite material comprising a polymer, a crosslinking agent that forms transient crosslinks between two or more polymer chains and a conductive nanomaterial, wherein the nanocomposite material is printed in the form of a film or a sheet. The crosslinking agent is a weak crosslinking agent forming non-covalent (non-permanent, temporary, transient, or temporal) crosslinks between polymer chains.

In one aspect, the film or sheet of printed nanocomposite material has a thickness of between about 5 nm to about 500 µm; that is about 5 nm, 10 nm, 20 nm, 30 nm, 40 nm, nm, 60 nm, 70 nm, 80 nm, 90 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, and 500 µm.

In one aspect, the film or sheet of printed nanocomposite material has a thickness of between about 150 nm and 10 µm.

In one aspect, the film or sheet of printed nanocomposite material has a thickness of between about 200 nm and 5 µm.

In one aspect, the conductive nanomaterial is selected from the group comprising graphene, reduced graphene oxide, metallic nano-particles (MNPs), metallic nano-platelets, metallic nanowires (MNWs), carbon fibres, carbon black, carbon nanotubes (CNTs), and multi-walled carbon nanotubes (MWCNTs).

In one aspect, the conductive nanomaterial is graphene.

In one aspect, the polymer is an elastomer selected from the group comprising polybutadiene, butadiene and acrylonitrile copolymers (NBR), natural and synthetic rubber, polyesteramide, chloropene rubbers, poly(styrene-b-butadiene) copolymers, polysiloxanes (such as polydimethylsiloxane (PDMS) (or silicone oil)), polyisoprene, polyurethane, polychloroprene, chlorinated polyethylene, polyester/ether urethane, polyurethane, polyethylene propylene, chlorosulphanated polyethylene, polyalkylene oxide, flurosilicone, highly saturated nitrile (HSN, HNBR), nitrile, polyacrylate, silicone, fluorinated ethylene propylene (FEP), a perfluoroelastomer, a fluroelastomer, a copolymer of tetrafluoroethylene/propylene, carboxylated nitrile, a dipolymer of hexafluoropropylene and vinylidene fluoride, and mixtures thereof. Preferably, the polymer is polydimethylsiloxane.

In one aspect, the polymer is a thermoplastic selected from the group comprising acrylonitrile butadiene styrene, polypropylene, polyethylene, polyvinylchloride, polyamide, polyester, acrylic, polyacrylic, polyacrylonitrile, polycarbonate, ethylene-vinyl acetate, ethylene vinyl alcohol, polytetrafluoroethylene, ethylene chlorotrifluoroethylene, ethylene tetrafluoroethylene, liquid crystal polymer, polybutadiene, polychlorotrifluoroehtylene, polystyrene, polyurethane, polyester resin, polysulfide, polyvinyl alcohol, polyvinyl chloride emulsion, polyvinylpyrrolidone, silicone, styrene acrylic copolymer, dichloromethane, cyanoacrylate, and polyvinyl acetate.

In one aspect, the polymer is a copolymer selected from the group comprising copolymers of propylene and ethylene, Acetal copolymers (Polyoxymethylenes), Polymethylpentene Copolymer (PMP), Amorphous copolyester (PETG), acrylic and acrylate copolymers, polycarbonate (PC) copolymer, Styrene block copolymers (SBCs) to include Poly(styrene-butadiene-styrene) (SBS), Poly(styrene-isoprene-styrene) (SIS), Poly(styrene-ethylene/butylene-styrene) (SEBS), Ethylene vinyl acetate (EVA), and ethylene vinyl alcohol copolymer (EVOH).

In one aspect, the printed nanocomposite material is coated with a polymer, a thermoplastic, an elastomer, a copolymer, or a combination thereof, to encapsulate the film or sheet. An example of the polymers that can be used are listed above, and also include, for example, where the encapsulating polymer used is an acrylate copolymer, or a silicone-based copolymer (such as SYLGARD®-184 silicone elastomer (a clear, two-component polydimethylsiloxane elastomer mixed in a 10:1 ratio (Dow Chemical Company))). The encapsulating polymer is applied after the printed nanocomposite material has dried.

The SYLGARD®-184 silicone elastomer is typically composed of Dimethyl Siloxane, Dimethylvinylsiloxy-terminated and Ethylbenzene which are mixed together in a 10:1 ratio and cured using Dimethylvinylated and Trimethylated Silica.

In one aspect, the polymer is a biopolymer selected from the group comprising gelatin, lignin, cellulose, polyalkylene esters, polyvinyl alcohol, polyamide esters, polyalkylene esters, polyanhydrides, polylactide (PLA) and its copolymers, and polyhydroxyalkanoate (PHA).

In one aspect of the present invention, there is provided a composite material produced by the process described herein selected from the group comprising a polydimethylsiloxane (PDMS)-graphene composite, a hydrogel-silver nanoplatelet composite, a polyester-graphene composite, a polyvinyl acetate-graphene composite, an acrylonitrile butadiene styrene-graphene composite, a polypropylene-graphene composite, a polyethylene-graphene composite, a polyvinylchloride-graphene composite, a polyamide-graphene composite, an acrylic-graphene composite, a polyacrylic-graphene composite, a polyacrylonitrile-graphene composite, a polycarbonate-graphene composite, an ethylene-vinyl acetate-graphene composite, an ethylene vinyl alcohol-graphene composite, a polytetrafluoroethylene-graphene composite, an ethylene chlorotrifluoroethylene-graphene composite, an ethylene tetrafluoroethylene-graphene composite, a polybutadiene-graphene composite, a polychlorotrifluoroehtylene-graphene composite, a polystyrene-graphene composite, a polyurethane-graphene composite, a polyvinyl acetate-graphene composite. It should be understood that the composite products listed above may have graphene substituted for any conductive nanomaterial, such as silver nano-platelets.

In one aspect, the crosslinking agent that forms transient crosslinks between two or more polymer chains is a weak-crosslinking agent. An example of a weak-crosslinking agent is boric acid.

In one aspect, the printed nanocomposite material described above consists of a low molecular weight polymer, a weakly crosslinking agent, and a conductive nanomaterial. Preferably, the polymer is low molecular weight polydimethylsiloxane, the weakly crosslinking agent is boric acid, and the conductive nanomaterial is graphene. The weakly crosslinking agent forms non-covalent (non-permanent, temporary, transient, or temporal) crosslinks between polymer chains.

In one aspect, the concentration of the conductive nanomaterial in the printed nanocomposite material is between about 0.01 vol. % to about 99 vol. %; preferably between about 0.01 vol. % to about 95 vol %; more preferably between about 0.01 vol. % to about 90 vol. %. In one aspect, the concentration of the conductive nanomaterial in the printed nanocomposite material is between about 0.01 vol. % to about 80 vol. %; between about 0.01 vol. % to about 75 vol. %; between about 0.01 vol. % to about 70 vol. %; between about 0.01 vol. % to about 65 vol. %; between about 0.01 vol. % to about vol. %; between about 0.01 vol. % to about 55 vol. %; between about 0.01 vol. % to about 50 vol. %; between about 0.01 vol. % to about 45 vol. %; between about 0.01 vol. % to about 40 vol. %; between about 0.01 vol. % to about 35 vol. %; between about vol. % to about 30 vol. %; between about 0.01 vol. % to about 25 vol. %; between about 0.01 vol. % to about 20 vol. %; between about 0.01 vol. % to about 15 vol. %; between about 0.01 vol. % to about 10 vol. %; and between about 0.01 vol. % to about 5 vol. %. In one aspect, the concentration of the conductive nanomaterial in the printed nanocomposite material is between about 5 vol. % to about 10 vol. %.

In one aspect, the printed nanocomposite material has a gauge factor of between 0.5 and 500. That is, between about 0.5, 0.6, 0.7, 0.8, 0.9, 1, 2, 3, 4, 5, 10, 15, 20, 25, 30, 40, 45, 50, 75, 100, 125, 150, 175, 200, 225, 250, 275, 300, 325, 350, 375, 400, 425, 450, 475, and 500.

In one aspect, the conducting nanomaterial resides on the surface of the sheet or film distal a substrate.

In one aspect, the sheet or film is encapsulated in a polymer, an elastomer, a thermoplastic, a copolymer, or a combination thereof. An example of said encapsulating polymer is an acrylate copolymer or an elastomer copolymer. In one aspect, the elastomer copolymer is SYLGARD®-184 silicone elastomer. The elastomer is also selected from the group comprising polybutadiene, butadiene and acrylonitrile copolymers (NBR), natural and synthetic rubber, polyesteramide, chloropene rubbers, poly(styrene-b-butadiene) copolymers, polysiloxanes (such as polydimethylsiloxane (PDMS) (or silicone oil)), polyisoprene, polyurethane, polychloroprene, chlorinated polyethylene, polyester/ether urethane, polyurethane, polyethylene propylene, chlorosulphanated polyethylene, polyalkylene oxide, flurosilicone, highly saturated nitrile (HSN, HNBR), nitrile, polyacrylate, silicone, fluorinated ethylene propylene (FEP), a perfluoroelastomer, a fluroelastomer, a copolymer of tetrafluoroethylene/propylene, carboxylated nitrile, a dipolymer of hexafluoropropylene and vinylidene fluoride, and mixtures thereof. The thermoplastic is selected from the group comprising acrylonitrile butadiene styrene, polypropylene, polyethylene, polyvinylchloride, polyamide, polyester, acrylic, polyacrylic, polyacrylonitrile, polycarbonate, ethylene-vinyl acetate, ethylene vinyl alcohol, polytetrafluoroethylene, ethylene chlorotrifluoroethylene, ethylene tetrafluoroethylene, liquid crystal polymer, polybutadiene, polychlorotrifluoroehtylene, polystyrene, polyurethane, polyester resin, polysulfide, polyvinyl alcohol, polyvinyl chloride emulsion, polyvinylpyrrolidone, silicone, styrene acrylic copolymer, dichloromethane, cyanoacrylate, and polyvinyl acetate. The copolymer selected from the group comprising copolymers of propylene and ethylene, Acetal copolymers (Polyoxymethylenes), Polymethylpentene Copolymer (PMP), Amorphous copolyester (PETG), acrylic and acrylate copolymers, polycarbonate (PC) copolymer, Styrene block copolymers (SBCs) to include Poly(styrene-butadiene-styrene) (SBS), Poly(styrene-isoprene-styrene) (SIS), Poly(styrene-ethylene/butylene-styrene) (SEBS), Ethylene vinyl acetate (EVA), and ethylene vinyl alcohol copolymer (EVOH).

In one aspect, there is provided a printed strain sensor comprising the printed nanocomposite material as describe above. In one aspect, the printed nanocomposite material is on at least a part of a surface of a substrate.

In one aspect, the substrate is selected from glass, semiconductors, metal, ceramic, aluminium foil, copper foil or other stable conductive foils or layers.

In one aspect, the substrate further comprises an adhesive on the substrate's surface without the printed nanocomposite material film.

In one aspect, the printed nanocomposite material is in the form of a film with a thickness of between 5 nm and 500 µm.; that is about 5 nm, 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, and 500 µm.

In one aspect, there is provided a method of manufacturing the printed strain sensor described above, the method comprising printing the nanocomposite material onto the substrate in the form of a film and drying the printed nanocomposite material.

In one aspect, the nanocomposite material is printed in the shape of a predetermined pattern.

In one aspect, the nanocomposite material is printed onto the substrate by screen or aerosol printing.

In one aspect, the method further comprises the step of applying a polymer, an elastomer, a thermoplastic, a copolymer, or a combination thereof to the printed nanocomposite material after drying to encapsulate the sheet or film. An example of said encapsulating polymer is an acrylate copolymer or a silicone-based copolymer (such as the SYLGARD®-184 silicone elastomer). The elastomer is selected from the group comprising polybutadiene, butadiene and acrylonitrile copolymers (NBR), natural and synthetic rubber, polyesteramide, chloropene rubbers, poly(styrene-b-butadiene) copolymers, polysiloxanes (such as polydimethylsiloxane (PDMS) (or silicone oil)), polyisoprene, polyurethane, polychloroprene, chlorinated polyethylene, polyester/ether urethane, polyurethane, polyethylene propylene, chlorosulphanated polyethylene, polyalkylene oxide, flurosilicone, highly saturated nitrile (HSN, HNBR), nitrile, polyacrylate, silicone, fluorinated ethylene propylene (FEP), a perfluoroelastomer, a fluroelastomer, a copolymer of tetrafluoroethylene/propylene, carboxylated nitrile, a dipolymer of hexafluoropropylene and vinylidene fluoride, and mixtures thereof. The thermoplastic is selected from the group comprising acrylonitrile butadiene styrene, polypropylene, polyethylene, polyvinylchloride, polyamide, polyester, acrylic, polyacrylic, polyacrylonitrile, polycarbonate, ethylene-vinyl acetate, ethylene vinyl alcohol, polytetrafluoroethylene, ethylene chlorotrifluoroethylene, ethylene tetrafluoroethylene, liquid crystal polymer, polybutadiene, polychlorotrifluoroehtylene, polystyrene, polyurethane, polyester resin, polysulfide, polyvinyl alcohol, polyvinyl chloride emulsion, polyvinylpyrrolidone, silicone, styrene acrylic copolymer, dichloromethane, cyanoacrylate, and polyvinyl acetate. The copolymer selected from the group comprising copolymers of propylene and ethylene, Acetal copolymers (Polyoxymethylenes), Polymethylpentene Copolymer (PMP), Amorphous copolyester (PETG), acrylic and acrylate copolymers, polycarbonate (PC) copolymer, Styrene block copolymers (SBCs) to include Poly(styrene-butadiene-styrene) (SBS), Poly(styrene-isoprene-styrene) (SIS), Poly(styrene-ethylene/butylene-styrene) (SEBS), Ethylene vinyl acetate (EVA), and ethylene vinyl alcohol copolymer (EVOH).

In one aspect, there is provided a method of measuring power output of a cyclist, the method comprising measuring a strain, using one or more printed sensors described above, exerted by a cyclist on a bicycle frame, wherein the one or more printed sensors are on the bicycle frame.

In one aspect, the one or more printed sensors are arranged on the bicycle frame in a predetermined pattern.

In one aspect, there is a method of measuring power output of a cyclist, the method comprising the step of applying one or more of the printed sensors described above to a frame of a bicycle, the frame comprising a seat tube, a bottom bracket shell, a top tube, a down tube, a chain stay, a seat stay and a head tube, wherein the printed sensors are placed on a lower segment of the seat tube above the join between the bottom bracket shell and the seat tube, wherein the oscillatory strains in the bicycle are maximised from the rotations of the pedals.

In one aspect, the printed strain sensor measures the power output and cadence of the user.

In one aspect, the predetermined pattern is a rectangular rosette, a delta rosette, or any shape required to cover an area over which the strain is likely to be distributed.

In one aspect, the strain exerted on the bicycle frame is measured in a uni-directional or a multi-directional manner.

In one aspect, the printed strain sensor further comprises a power source, circuitry to measure its resistance and a means to control the sensor and record readings. In other aspects of any embodiment described here, the printed strain sensor can further comprise a wireless technology for exchanging data between the printed strain sensor and a device over short distances using, for example, short-wavelength UHF radio waves (for example, BLUETOOTH®), other wireless data transmission methods such as wireless mesh networks targeted at battery-powered devices in wireless control and monitoring applications (such as ZIGBEE®), local area networking of devices and Internet access (such as WIFI®), and other wireless communications protocols using a mesh network using low-energy radio waves to communicate from appliance to appliance (such as Z-WAVE®). Typically, a remote app is required on the device to record the readings from the printed strain sensor.

In one aspect, there is provided an insole comprising a plurality of printed sensors applied to the surface of the insole, the sensors comprising the printed nanocomposite material as described above.

In one aspect, the insole is encapsulated in a polymer or copolymer. Typically, the encapsulating polymer is an acrylate copolymer or a silicone-based copolymer (for example, a covalently crosslinked PDMS such as the SYLGARD®-184 silicone elastomer).

In one aspect, the printed sensor applied to the flexible insole further comprises a power source, circuitry to measure its resistance, and a means to control the sensor and record readings.

In one aspect, the insole further comprises a battery arranged to connect to the circuitry of the printed sensor.

In one aspect, the insole further comprises a microprocessor or microcontroller for receiving each metric data signal generated from each sensor on the surface of the insole. In one aspect, the microcontroller is single-board microcontroller (including a microprocessor, Input/Output circuits, a clock generator, random-access memory (RAM), stored program memory and any necessary support integrated circuits (ICs)) such as an Arduino microcontroller.

In one aspect, the printed sensors are positioned on the surface of the insole to correspond to the heel, the mid foot and the fore foot of the user's foot.

In one aspect, the printed sensors are positioned to correspond to at least the first metatarsal head, the second metatarsal head, the third metatarsal head, the fourth metatarsal head, the fifth metatarsal head, the space between the second metatarsal head and the third metatarsal head, and the big toe of said foot, or a combination thereof.

In one aspect the printed sensors are positioned to correspond to the first metatarsal (big toe), the fifth metatarsal (little toe), and at the Calcaneus (heel).

In one aspect, the printed sensors are positioned to correspond to the five distal phalanges (tips of toes), along first to fifth metatarsals (where toes meet the "ball" of the foot), at least two sensors along the length of the cuboid (outside midfoot), at least two sensors along the medial cuneiforms (inside midfoot), and at least one sensor at the calcaneus (heel). Preferably, there is at least three sensors along the length of the cuboid (outside midfoot), at least three sensors along the medial cuneiforms (inside midfoot), and at least two sensors at the calcaneus (heel).

In one aspect, the insole is flexible or inflexible, or combination thereof.

In one aspect, there is provided a method of measuring a force generated by a user engaged in running or walking, the method comprising measuring a force applied by the user's foot to one or more printed sensors of as described above present inside a shoe worn by the user.

In one aspect, there is a method of measuring a force generated by a user engaged in running or walking, the method comprising the steps of:
  applying at least one pressure sensor on the surface of an insole for a shoe, the pressure sensor comprising the printed nanocomposite material described herein,
  inserting the insole into the user's shoe so that the sensors are adjacent the foot of the user;
  measuring the force generated by the user when the user's foot applies the force to the sensor with each step; and
  processing said force data and comparing said force data against a baseline reading to determine a metric of interest. The method can use this baseline reading to determine where the metric for the user falls when compared to the baseline, so that aspects of the user's health can be monitored. The data can be used to determine biomechanical and biochemical parameters of the user. The biochemical parameters include calorie expenditure, for example.

In one aspect of any one of the embodiments of the methods above, the metric is selected from force distribution, power, cadence, distance, time, pace, splits elevation, calories, cadence, step length, foot strike, pronation, or a combination thereof.

In other aspects of any embodiment described here, the printed strain sensor can further comprise a wireless technology for exchanging data between the printed strain sensor and a device over short distances, using for example short-wavelength UHF radio waves (for example, BLUETOOTH®), other wireless data transmission methods such as wireless mesh networks targeted at battery-powered devices in wireless control and monitoring applications (such as ZIGBEE®), local area networking of devices and Internet access (such as WIFI®), and other wireless communications protocols using a mesh network using low-energy radio waves to communicate from appliance to appliance (such as Z-WAVE®). Typically, a remote app is required on the device to record the readings from the sensor composed of the printed nanocomposite material of the claimed invention.

The printed nanocomposite material of the claimed invention can also be used as a printed sensor in non-invasive wearable devices for use in, for example, monitoring human blood biochemistry; measuring athlete performance through eccrine sweat, heart rate variability (HRV), galvanic skin response, blood glucose levels, and saliva; and stress levels in a wearer.

The advantages of the printed nanocomposite material and devices of the claimed invention are, for example, the high sensitivity of a device coupled with an electrical conductivity high enough that it can be integrated with other electronic components into a fully functional device. Typically for most strain sensors, the conductivity of the device is inversely proportional to the sensing ability. The printed nanocomposite material of the claimed invention is unique in the sense that it can maintain a high degree of sensitivity with a workable electrical conductivity. The printed nanocomposite material exhibits strain-rate independent sensitivity. Further, the versatility of manufacturing methods available (screen printing, aerosol deposition, mechanical deposition, and the like) while maintaining similar electrical and sensing characteristics has hitherto never been described. The ability to print the printed nanocomposite material of the claimed invention onto a variety of substrates (stiff or flexible) allows a device to be mounted to curved surfaces and function without any significant changes to the device's performance. The cost of the individual device is extremely low compared to existing devices which claim a similar sensitivity. In certain aspects, the device can be self-adhering allowing it to be mounted without any additional adhesive necessary. In other aspects, the device of the claimed invention can have adhesive applied to it or the device can be printed on an adhesive layer.

These devices created using the nanocomposite material of the claimed invention have a very broad range of applications.

Medical Applications: The invention discussed above has the potential to be used as a non-invasive diagnostic tool for real-time health monitoring and evaluation. Preliminary tests have shown the invention's ability to detect both pulse and breathing patterns in human subjects. The strain-rate and frequency independent sensitivity of the material makes it ideal for monitoring vital signs. In addition to the strain rate/frequency independence, the high sensitivity of the material would allow the device to be used in a range of high precision measurements as part of the physician's diagnosis procedure. An example of this would be the in monitoring the onset and progression of symptoms in patients with degenerative diseases which have subtle physical cues as early symptoms. This can occur in the forms of tremors which depending on the cause may or not be life threatening. "Neurological tremor" is a movement disorder which affects more than 4% of the elderly population and is characterised as a non-linear, non-stationary physical phenomenon. Although this particular tremor is not-life threatening, it is a chronic condition which can have implications for the long-term care required for elderly patients. Another example is a tremor known as "Essential tremor" which is an early symptom of Parkinson's dieses. In this case the condition is life threatening meaning early detection is crucial. The magnitude of tremors in patients over time can be an indicator of both the onset of the disease and ongoing patient health. These wearable sensors would allow the magnitude of tremors to be quantitatively measured and provide insight into patient progress, allowing for both a diagnosis to be made in addition to informing physicians about patient progress, facilitating appropriate care decisions to be made. Several groups have focused on measuring both the onset and progression of these tremors using a variety of strain sensing devices. Physiotherapy and physical rehabilitation are other potential areas of application. By mounting the device to a patient's shoes or foot, it would be possible to determine where pressure is being applied which can then be used to evaluation a patient's gait—a key indicator of a number of biomechanical issues. This information can be used by the physician to determine underlying issues in the case of injury as well as a tool for analysis a patient's progress during a rehabilitation program. The invention could also be used in the shoes of a wearer to determine if the wearer has taken a fall. If the wearer does fall, an alarm could be sounded on a device carried by a carer, or by a health facility that is monitoring the wearer via the sensor, alerting them to the fall and any potential negative outcome arising from the user's fall. Other uses include measuring a patient's ability to swallow and diagnosing dysphagia (inability to swallow) which is a common issue for victims of stroke. Further uses include monitoring contractions during the late stages of pregnancy to identify false labour (Braxton Hicks contractions) as well as the progress of true labour by determining the frequency of contractions.

Wearable Consumer Electronics: The device's versatility allows it to be potentially used in a wide range of applications especially in the emerging market of wearable consumer electronics. Possible examples include real time breathing and pulse monitors for consumers engaging in exercise. A specific example of a potential application for both professional and recreational athletes is a bike power meter device using the printed nanocomposite material of the invention described above. In this instance, the printed nanocomposite material is printed as a strain sensing device that is positioned on the lower segment of the seat tube of the bicycle frame. This is in most cases just above the join between the bottom bracket shell and the seat tube of the bicycle frame. They are typically placed on the side of the frame so that the longitudinal strains due to lateral deflection can be measured appropriately. In most cases, this is also centred along the neutral axis of the seat tube (neutral axis when considering vertical frame deflection). The exact position in the region described can be determined using Finite Element Analysis or other techniques. This will depict the exact position that deflects laterally due to the forces applied at the pedals of the bicycle and not any other forces applied to the bicycle frame.

Mechanical Diagnostics: The printed strain device of the claimed invention has the potential, due to its high sensitivity and ability to be adhered to both flat and curved surfaces, to be used in the area of mechanical diagnostics. The device would be capable of measuring both the magnitude of the strain going through the materials as well as the time frame over which the strain happens—this could be a useful diagnostic tool for automotive engineers in the area of impact testing. This invention allows for the making of large area strain sensors quickly and cheaply. In the area of impact sensing, with the appropriate electronics, it would be possible to obtain the area of which the stress is distributed upon impact.

Other Applications: The printed device of the claimed invention also has other applications such as determining the strain and movements of structures such as buildings, bridges, roads, paving, vehicles, dams, hulls/masts of ships, oil drilling platforms, wings/fuselage of planes, train rails, fans (turbines, cooling systems, windfarms), bridge cables, and the like.

The rosette pattern of printed sensors describes two possible arrangements of sensors—rectangular and delta configurations. In the rectangular configuration there are three strain gauges. Two of the gauges are place at a 90° angle on an XY-axis with the third strain gauge place in between the other two at an angle of 45°. The delta configuration consists of three strain gauges. The strain gauges are arranged as an equilateral triangle with an angle of 60 degrees between each of the gauges. In addition to this it is also possible to print arrays of the nanocomposite material of the claimed invention (not necessarily in the pattern of the metal foil gauge) with regular intervals between the deposited material in order to measure the area over which strain is distributed in a material. These arrays could be any shape depending on the area over which the strain is likely to be distributed.

Definitions

The term "polymer" in the specification should be understood to mean a large molecule (macromolecule) composed of repeating structural units. These subunits are typically connected by covalent chemical bonds. Although the term "polymer" is sometimes taken to refer to plastics, it actually encompasses a large class comprising both natural and synthetic materials with a wide variety of properties. In the specification, such polymers are synthetic and naturally occurring elastomers. Such polymers may be thermoplastics, elastomers, or biopolymers.

The term "copolymer" should be understood to mean a polymer derived from two (or more) monomeric species, for example a combination of any two of the below-mentioned polymers. An example of a copolymer, but not limited to such, is PETG (Polyethylene Terephthalate Glycol), which is a PET modified by copolymerization. PETG is a clear amorphous thermoplastic that can be injection moulded or sheet extruded and has superior barrier performance used in the container industry.

In the specification, the term "low molecular weight polydimethylsiloxane (PDMS)" should be understood to mean a PDMS polymer with relatively short chain length. Ideally this would refer to molecular weights below the critical molecular weight for entanglement. PDMS is also known as silicone oil. The two terms can be used interchangeably.

In the specification, the term "cross-link", "cross-linked" or "crosslink" should be understood to mean a bond that links one polymer chain to another. They can be van der Waals, covalent bonds or ionic bonds. The crosslinking of polymers via covalent bonds are typical of the cross-links formed in US 2014/011969 A1 and US 2016/033403 A1. Such covalently bonded crosslinks produce very rigid, inflexible crosslinked polymers (materials). They create bonds between polymer chains or between polymers and embedded particles which are permanent and very strong. For example, if two short chain PDMS molecules (e.g., silicone oil) were covalently crosslinked, they would make a longer chain PDMS molecule with none of the character of the short chains remaining. Such covalently bonded crosslinked polymers are strong and permanent. These types of cross-linked polymers are unsuitable for use in the devices and composite materials described herein.

In the specification, the term "non-covalent crosslink", "weak crosslink", "weakly crosslinked", "transient crosslink", or "temporary crosslink", all of which can be used interchangeably, should be understood to mean when a cross linking agent connects two polymer chains via weak, non-covalent bonds, such as hydrogen bonds or dipolar interactions These links are transient, lasting typically about 1 second before they break. They can later reform in the same place or elsewhere within the matrix. The key fact is that while broken, the polymer chains can move relative to their original positions. This results in very low viscosity (i.e., low for a solid, between about 50 to about 11,000 Pa s). The physical properties (viscosity and sensitivity) of a polymer with non-covalent cross-link bonds are significantly very different to a polymer with permanent or covalent cross-linked bonds. These types of non-covalent cross-linked polymers are suitable for use in the devices and composite materials described herein. Covalently crosslinked silicones deform elastically, while temporally (weakly) crosslinked silicones deform viscoelastically.

In the specification, the term "weak cross-linking agent" should be understood to mean a cross-linking agent that forms transient or non-covalent crosslinks between at least two polymer chains. The weak crosslinking agent creates links that are transient, lasting typically about 1 second before they break. The crosslinks can later reform in the same place or elsewhere within the matrix. The key fact is that while broken, the polymer chains can move relative to their original positions.

In the specification, the term "low viscosity" should be understood to mean a non-covalent cross-linked polymer, without the addition of a conductive nanomaterial, having a viscosity no higher than about 11,000 Pa s and no lower than about 50 Pa s. Ideally, the non-covalent cross-linked polymer with low viscosity has a viscosity no higher than about 10,000 Pa s and no lower than about 100 Pa s; that is, between about 100, 110, 120, 130, 140, 150, 160, 170, 180, 190, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 790, 800, 820, 840, 860, 880, 900, 920, 940, 960, 980, 1000, 1200, 1400, 1600, 1800, 2000, 2200, 2400, 2600, 2800, 3000, 3200, 3400, 3600, 3800, 4000, 4200, 4400, 4600, 4800, 5000, 5200, 5400, 5600, 5800, 6000, 6200, 6400, 6600, 6800, 7000, 7200, 7400, 7600, 7800, 8000, 8200, 8400, 8600, 8800, 9000, 9200, 9400, 9600, 9800, 10000, 10200, 10400, 10600, 10800, 11000 Pa s.

In the specification, the term "high viscosity" should be understood to mean a covalent cross-linked polymer, without the addition of a conductive nanomaterial, having a viscosity higher than about 11,001 Pa s.

In the specification, the term "nanomaterial" should be understood to mean conductive materials of which a single unit is sized (in at least one dimension) of between 1 to 100 nm measured in kelvin. Examples of nanomaterials include graphene, reduced graphene oxide, metallic nano-particles (MNPs), metallic nano-platelets, metallic nanowires (MNWs), carbon fibres, carbon black, carbon nanotubes (CNTs), and multi-walled carbon nanotubes (MWCNTs). Reduced graphene oxide is prepared from reduction of graphene oxide by thermal, chemical or electrical treatments to reduce the oxygen content.

In the specification, the term "metallic nano-particles (MNPs)" should be understood to mean nanosized metals with dimensions (length, width or thickness) within the size range of 1-100 nm. Examples of such MNPs are silver or gold nanoparticles.

In the specification, the term "metallic nano-platelets" should be understood to mean nanosized metals formed as a sheet with diameters ranging from sub-micron to 100 microns, and 1 to 100 nm thick. The most common examples of such platelets are silver nano-platelets.

In the specification, the term "metallic nanowires (MNWs)" should be understood to mean nanosized metallic structures with a diameter within the size range of nanometers. It can also be defined as the ratio of the length to width being greater than 1000. Alternatively, nanowires can be defined as structures that have a thickness or diameter constrained to tens of nanometers or less and an unconstrained length. Examples of such MNWs are silver nanowires, nickel nanowires, platinum nanowires, gold nanowires, and bi- or tri-elemental nanowires made from alloys or core-shell structures.

In the specification, the term "gauge factor" should be understood to mean the relative change in electrical resistance R of a material, to the mechanical strain 6.

In the specification, the term "film" or "sheet" should be understood to mean thin, flat piece of material that is thin in comparison to its length and breadth. In an embodiment of one or more aspects of the invention, it is possible to pass from one point of it to any other point without leaving the surface of the film or sheet. The film or sheet can come in the form of continuous thin strips that form serpentine patterns or other patterns that are suitable for the purpose of measuring resistance.

In the specification, the term "printed" should be understood to mean any liquid phase deposition or printing method such as screen printing, ink jet printing, aerosol jet printing, gravure printing, 3D printing, spraying (electrospray, ultrasonic-spray, conventional aerosol spray) and mechanical deposition such as slurry casting, blade coating, filtration, flexography, roll-to-roll coating or processing, or drop casting.

In the specification, the term "bicycle" should be understood to mean a stationary and non-stationary bicycle.

BRIEF DESCRIPTION OF THE DRAWINGS

The invention will be more clearly understood from the following description of an embodiment thereof, given by way of example only, with reference to the accompanying drawings, in which:—

FIG. 5 illustrates comparative results using G-putty and a strain sensor of the claimed invention that was screen printed. a) is a comparison of the mechanical hysteresis curves of bulk graphene-polysilicone mixture (G-putty) (grey) to a rectangular sensor of the claimed invention screen-printed using the nanocomposite ink onto a PDMS substrate (blue). (b) compares the electrical hysteresis (how the fractional change in resistance changes with strain over one mechanical cycle) curves of bulk G-putty (grey) to a rectangular sensor of the claimed invention screen printed using the nanocomposite ink onto a PDMS substrate (blue). (c) is a comparison of the area contained within the hysteresis curve for the bulk G-putty and the screen-printed sensors of the claimed invention as a function of the strain rate during the mechanical tests. (d) is a comparison between the values of the gauge factor obtained for the bulk G-putty and the screen-printed sensors of the claimed invention as a function of the strain rate during testing. (e) shows the electrical response to a repeating sinusoidal strain of the screen-printed sensors of the claimed invention. The top panel show how the material is strained with time with the bottom panel showing the electromechanical response of the material. The response is in phase and consistent in amplitude during the testing. (f) is a comparison between the values of gauge factor obtained for bulk G-putty and the screen-printed sensors of the claimed invention as a function of the frequency that the material was cycled at.

FIG. 6 illustrates comparative results using G-putty and a strain sensor of the claimed invention that was aerosol jet (optomec) printed. a) is a comparison of the mechanical hysteresis curves of bulk graphene-polysilicone mixture (G-putty) (grey) to a rectangular sensor of the claimed invention optomec printed using the nanocomposite ink onto a PDMS substrate (gold). (b) compares the electrical hysteresis (how the fractional change in resistance changes with strain over one mechanical cycle) curves of bulk G-putty (grey) to a rectangular sensor of the claimed invention optomec printed using the nanocomposite ink onto a PDMS substrate (gold). (c) is a comparison of the area contained within the hysteresis curve for the bulk G-putty and the optomec printed sensors of the claimed invention as a function of the strain rate during the mechanical tests. (d) is a comparison between the values of the gauge factor obtained for the bulk G-putty and the optomec printed sensors of the claimed invention as a function of the strain rate during testing. (e) shows the electrical response to a repeating sinusoidal strain of the optomec printed sensors of the claimed invention. The top panel show how the material is strained with time with the bottom panel showing the electromechanical response of the material. The response is in phase and consistent in amplitude during the testing. (f) is a comparison between the values of the gauge factor obtained for bulk G-putty and the optomec printed sensors of the claimed invention as a function of the frequency that the material was cycled at.

DETAILED DESCRIPTION

The inventors have developed a method to formulate graphene (G)-putty-based inks which can be printed into directly patterned thin films on elastic substrates, significantly reducing hysteresis and rate-dependence. The inventors have fabricated such films into high-performance sensors which can be used in a number of applications, for example mounted on bicycles as velocity and power monitors.

Figure 1:
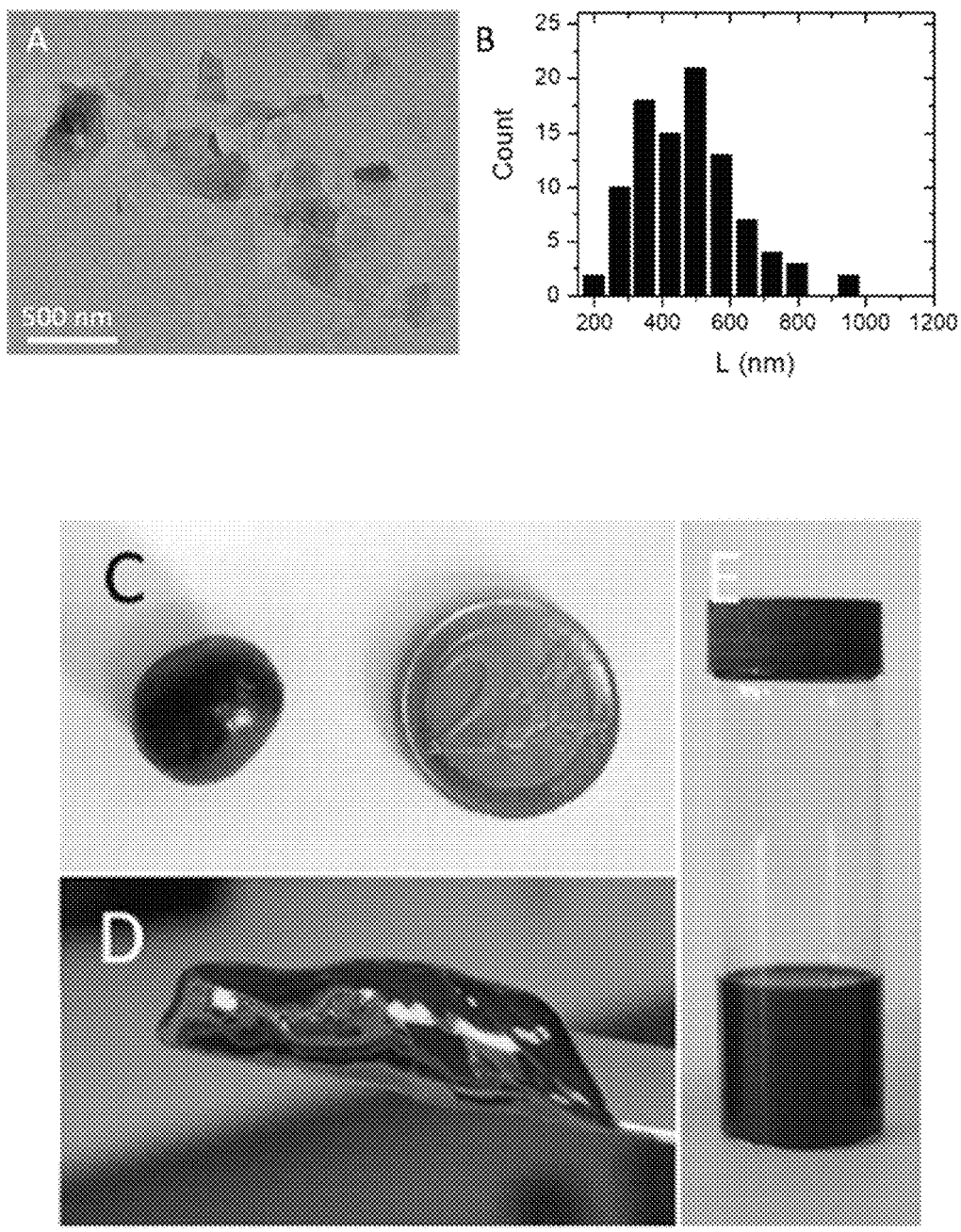
FIG. 1 illustrates the formulation and printing of a graphene-polysilicone mixture (G-putty) ink. a) Transmission Electron Microscopy (TEM) image of graphene used in G-putty fabrication. b) histogram of length of nanosheets observed in TEM images. c-e) Photographs of bulk G-putty (c), a paste of G-putty dissolved in a small amount of butanol (d) and a liquid ink prepared by dispersing bulk G-putty in isopropanol (e). f) Rheology measurements for butanol-based inks at various concentrations (corresponding to G-putty mass divided by solvent volume). Note that the two highest concentration samples are pastes. g-i) Photographs of thin films of G-putty prepared by spraying (g), screen-printing (h) and aerosol-jet printing (i). j) Thermogravimetry measurements for bulk G-putty, a film of G-putty formed by drop-casting ink into a Teflon tray and a sprayed G-putty film. k-m) SEM images of the surface of G-putty films prepared by spraying (k), screen-printing (l) and aerosol-jet printing (m).
Figure 1:
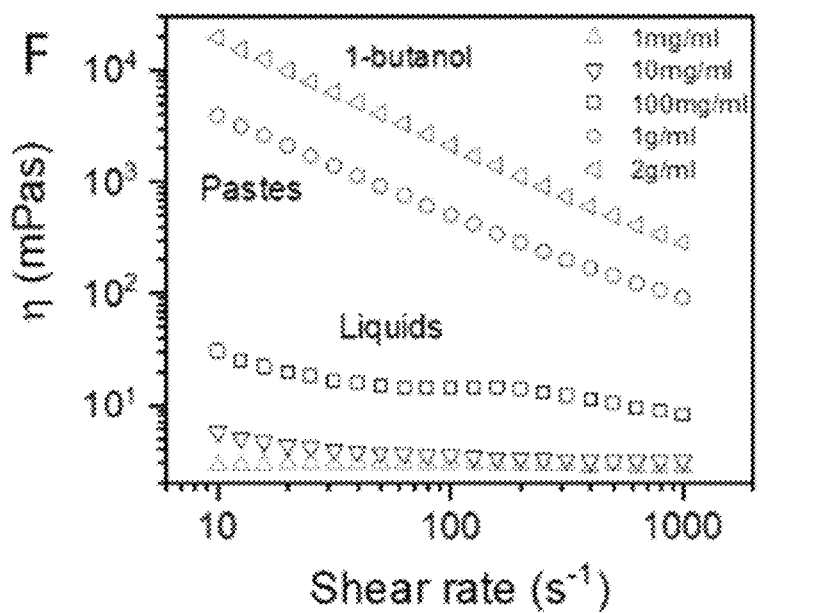
Figure 1:
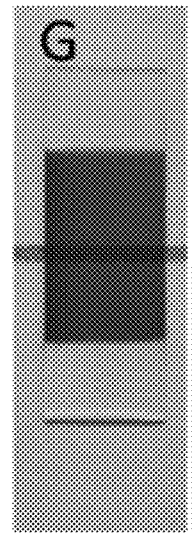
Figure 1:
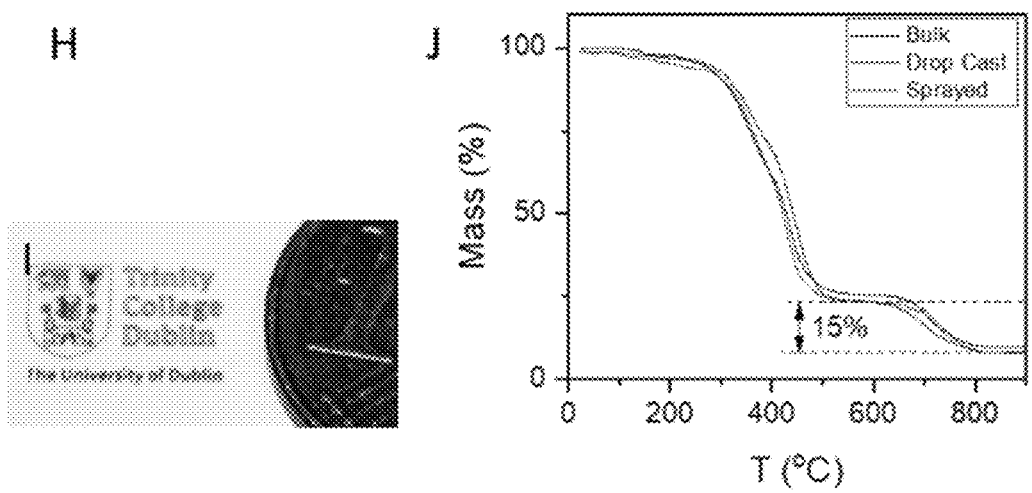
Figure 1:
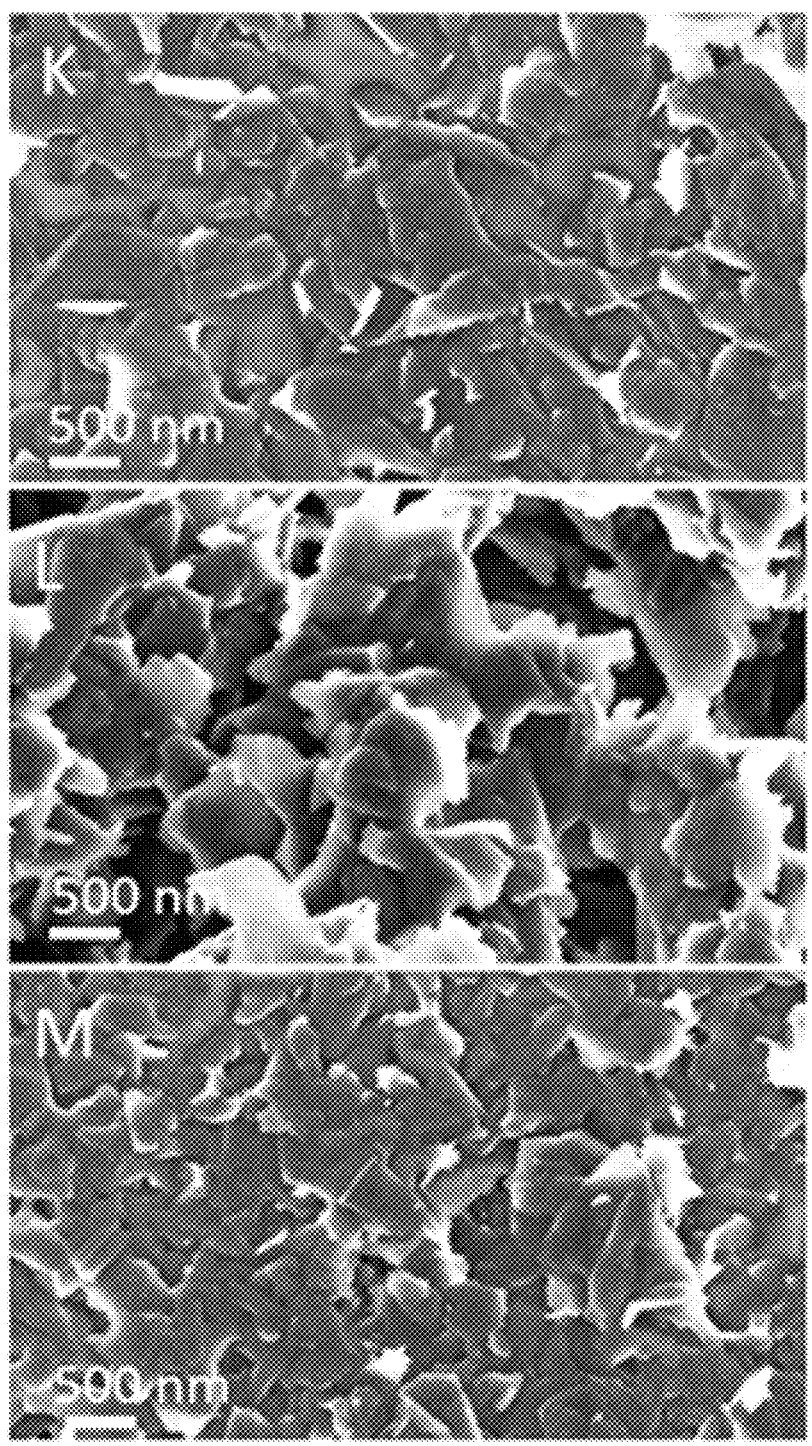

The hysteresis problems described above were resolved by printing G-putty as thin films on elastic substrates. The mechanical properties of these thin films are dominated by the substrate, frustrating the relaxation of the G-putty. To achieve this, the inventors used liquid-exfoliated graphene nanosheets (FIG. 1a) with a typical size of ~500 nm (FIG. 1b) to prepare G-putty (FIG. 1c) which was then ultrasonically dispersed in solvents such as butanol and isopropanol. Depending on the solvent volume used, the inventors could obtain pastes (FIG. 1d) or liquid inks (FIG. 1e) with viscosities which varied over >3 orders of magnitude (FIG. 1f). Access to such a viscosity range is important as screen printing pastes require viscosities of 1-1000 Pas, while inkjet printing employs inks of much lower viscosities (4-30 mPas). By tuning the solvent used and paste/ink concentration, the inventors could print thin films of G-putty via spray coating, screen-printing and aerosol-jet printing (FIGS. 1g-i). Importantly, screen- and aerosol-jet printing allow patterning during film formation. In all cases, the films appear uniform while thermogravimetric (TGA) measurements (FIG. 1j) show printed films to have graphene contents very close to that of the bulk G-putty. SEM measurements (FIGS. 1k-m) show the film surfaces to be rich in nanosheets with relatively small amounts of polymer present, suggestive of a partial polymer-nanosheet phase separation on deposition.

Although butanol and isopropanol are mentioned as possible solvents, other solvents that are suitable for use in making the nanocomposite material should have a boiling point of between about 40° C. to 120° C., such as, for example, chloroform, acetone and ethanol. The drying effect of the evaporating solvent play a role in determining the morphology of the film i.e., the rate at which the solvent evaporates.

Electrical measurements were performed for a range of graphene loadings in sprayed G-putty films, as well as for the bulk G-putty, which had been used to prepare the inks. The resultant conductivities are plotted versus graphene volume fraction, $\phi$, in FIG. 2a. Both data sets are consistent with the percolation theory which describes the $\phi$-dependence of the conductivity: $\sigma=\sigma_0(\phi-\phi_c)^n$. As shown in the panel, the percolation exponent, n, falls while $\sigma_0$ increases going from bulk to thin film, behaviour which is consistent with the reduction of inter-nanosheet tunnelling resistances. As a result, the sprayed G-putty displays very high conductivity, at least $1 \times 10^6$ higher than the bulk material, consistent with the idea of a graphene-rich surface region with reduced amounts of polymer separating the nanosheets. This is of great practical importance as it allows films of a given sheet resistance (e.g., for a given application) to be prepared with sprayed G-putty at much lower thickness than would be possible with the bulk material.

Figure 2:
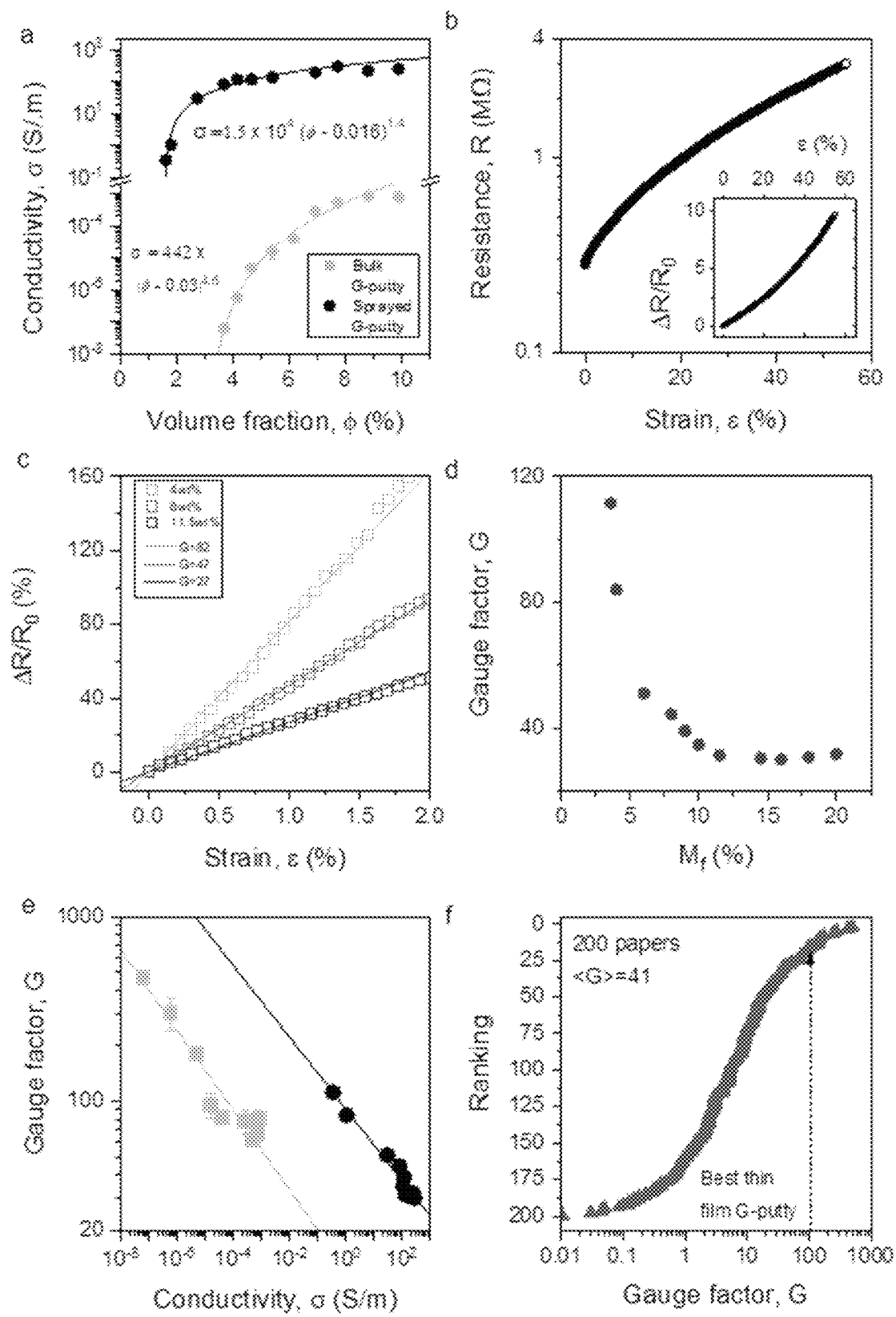
FIG. 2 illustrates the electromechanical properties of sprayed graphene-polysilicone mixture (G-putty) films. a) Conductivity plotted as a function of graphene volume fraction for bulk and sprayed G-putty. The solid lines are fits to percolation theory with fit parameters given in the panel. b) Resistance-strain curve (inset fractional resistance change) for sprayed G-putty (Mf=15 wt %). c) Fractional resistance change vs. strain for sprayed G-putty of three different mass fractions. d) Gauge factor versus mass fraction for spray cast G-putty. e) Gauge factor vs. conductivity for both bulk and sprayed G-putty, each for various values of $M_f$. f) Ranking (ordered from lowest gauge factor to highest gauge factor) versus reported value of low-strain G for data extracted from 200 published papers (see Boland, C. S. Stumbling Through the Research Wilderness, Standard Methods to Shine Light on Electrically Conductive Nanocomposites for Future Health-Care Monitoring. arXiv:1910.07249 (2019)). Plotted this way, the curve represents the cumulative distribution function[20] of the set of published gauge factor values.

This high conductivity is particularly important for the development of printed, thin film, G-putty-based strain sensors. Shown in FIG. 2b is data for electrical resistance as a function of applied tensile strain for an ~1μm thick film of G-putty ($M_f$=15 wt %) sprayed on a thin PDMS support. As observed in many nanocomposites, the resistance increases steadily with strain, accumulating a ×10 resistance change at 50% strain (see inset). It was noted that $\Delta R/R_0$ scales linearly with $\varepsilon$ up to ~25%, much higher than can be achieved with graphene-only networks. This well-defined resistance-strain relationship allows such materials to be used to sense strain. Graphs of $\Delta R/R_0$ versus $\varepsilon$, in the low strain region, are shown in FIG. 2c for sprayed G-putty films with three different graphene mass fractions. Average gauge factors are plotted versus graphene mass fraction in FIG. 2d and show the usual increase with decreasing filler loading, reaching gauge factor ~110 for mass fractions below 5%.

It has previously been reported that strain sensors often show negative correlations between conductivity and gauge factor. As shown in FIG. 2e, this is also the case for both bulk and sprayed G-putty. However, this graph clearly highlights the differences between these systems and shows that sprayed G-putty can achieve a given G at much higher conductivity than bulk G-putty. To put these values of gauge factor in perspective, in FIG. 2f literature data for 200 nanocomposite gauge factors (as originally reported in Boland et al. 2019) was plotted against their ranking (from worst to best). It was found that the best sprayed data from FIG. 2d to be well within the top 10% gauge factors.

Figure 3:
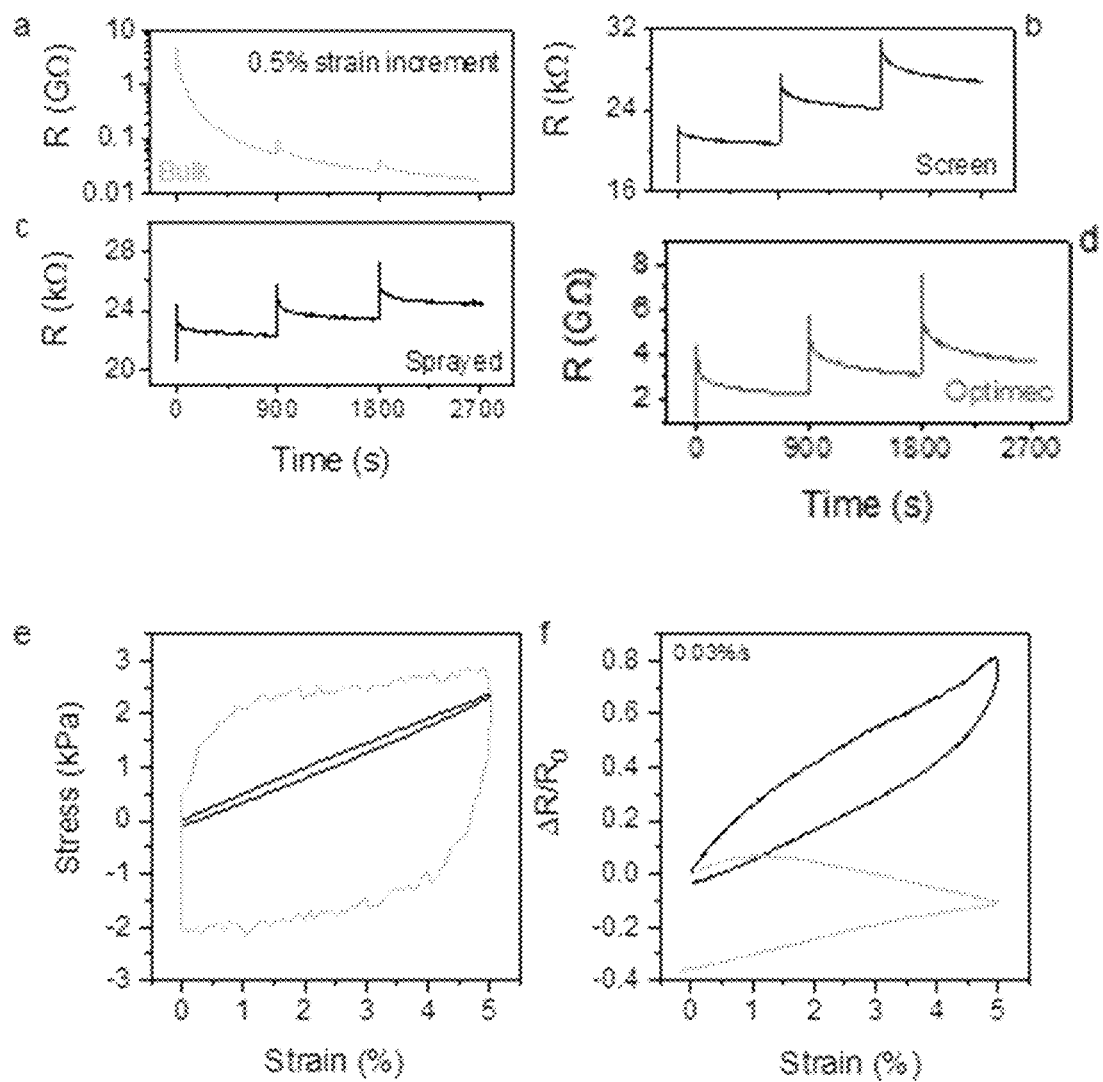
FIG. 3 illustrates the time- and rate-dependent properties of a graphene-polysilicone mixture (G-putty). a-d) Resistance versus time for bulk (a), screen printed (b), sprayed (c) and aerosol jet-printed (d) G-putty. In each case the sample was exposed to three successive 0.5% strain increments at 0, 900 and 1800 s. e) Stress strain curves (including strain release) for sprayed and bulk G-putty. f) Fractional resistance-change vs. strain curves (including strain release) for sprayed and bulk G-putty. g-h) Resistance hysteresis (g) and Gauge factor (h) plotted versus strain rate for bulk and sprayed G-putty. i-j) Strain (i) and resistance (j) vs. time for sprayed G-putty deformed using sinusoidal strains at 0.1 Hz. k) Oscillatory gauge factor versus frequency for bulk and sprayed G-putty.
Figure 3:
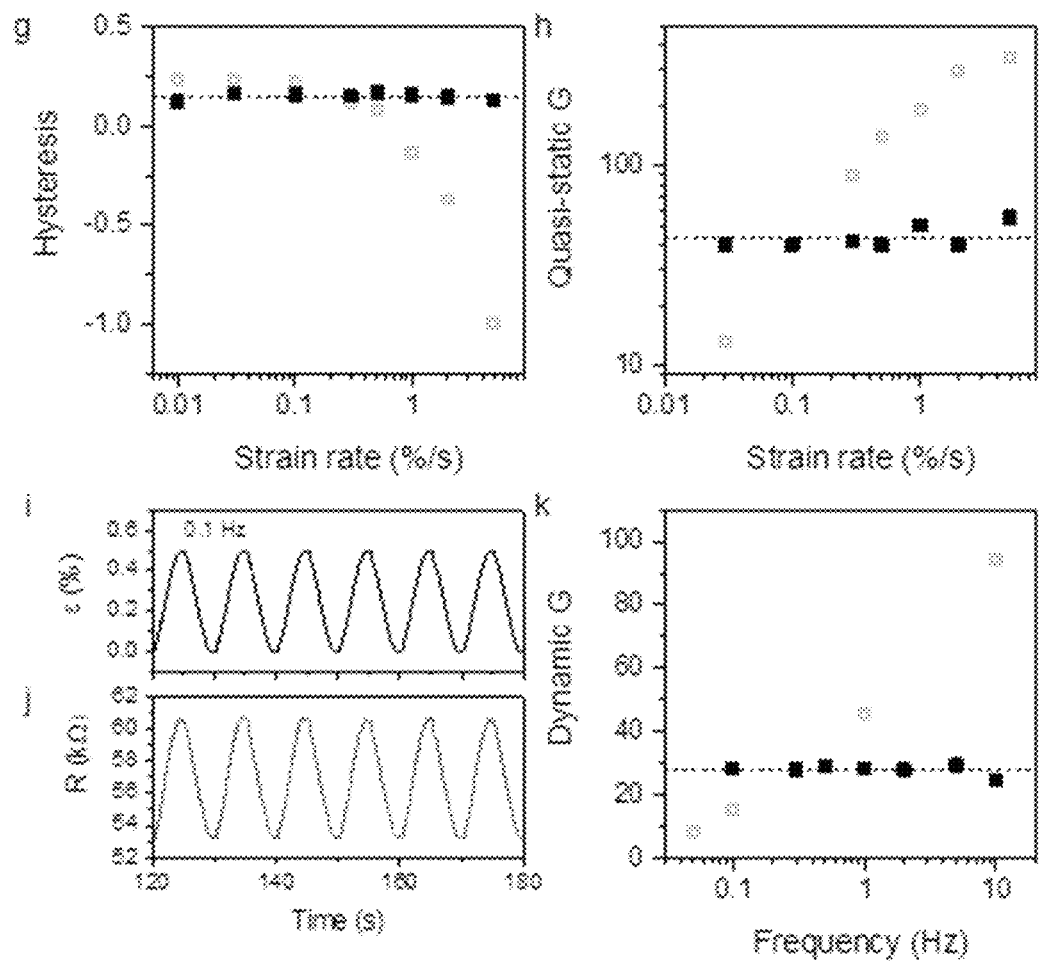

However, as indicated above, the biggest problem with bulk G-putty sensors is not their relatively low conductivity but the fact their extreme softness allows the graphene network to relax under strain. Such relaxation can be seen in the step strain experiment shown in FIG. 3a where the bulk G-putty was stretched to 0.5% strain and held before stretching again to 1% strain after 900 s and again held until 1800 s when it was stretched again to 1.5%. While a perfectly elastic conductor would show the resistance increasing as a "staircase", the bulk-G-putty shows sharp resistance increases followed by dramatic decays as the graphene network relaxes in the ultra-soft matrix. However, the inventors found that printed thin films of G-putty show much more staircase-like behaviour, albeit with short-lived relaxation effects at step edges (FIGS. 3b-d). The inventors' hypothesis that the thinness of the printed films means that the thin film is pinned at the substrate-film interface resulting in severely reduced relaxation.

As a result, the mechanical response of the system is dominated by the substrate. This is demonstrated in FIG. 3e. While the extreme viscoplastic_response of bulk G-putty results in very large stress-strain hysteresis in bulk G-putty (FIG. 3e), the thin film of G-putty sprayed onto PDMS shows near elastic behaviour with minimal hysteresis. One would expect the latter behaviour to allow effective practical strain sensing.

To test this, strain was applied and then released for a number of samples at various strain rates. As illustrated in FIG. 3f, for bulk G-putty the hysteresis is so severe that, after unloading, the resistance is well below the initial resistance. In contrast, for the sprayed film, although hysteresis is present, it is greatly reduced with the resistance returning to its initial value. Having defined the hysteresis as the area of the hysteresis loop divided by the area under the R-strain curve associated with the loading cycle, the hysteresis versus strain rate for bulk G-putty as well as sprayed films was plotted in FIG. 3g. For bulk G-putty, the hysteresis was very large and strain-rate dependent, varying from 0.25 to −1 (the sign is negative if the resistance is higher in the unload cycle compared to the load cycle). However, for the printed films, the hysteresis was much lower (~0.15) and virtually rate independent.

Such low hysteresis and rate-independence is critical for practical sensors where the relationship between resistance and stain must be similar under all circumstances. The invariance of the response of printed, thin-film G-putty can be seen by plotting the measured quasi-static gauge factor as a function of strain rate for spray-coated sensors in FIG. 3h with bulk G-putty data shown for comparison. While the bulk G-putty shows very significant rate dependence, the sprayed sensor shows almost perfect rate independence.

Such rate independence suggests that the oscillatory response of printed G-putty will also be frequency independent. To test this, strains oscillating between 0 and 0.5% at various frequencies were applied to sprayed G-putty as well as bulk G-putty (see FIGS. 3i-j). Again, while the dynamic gauge factor varied significantly with frequency for the bulk G-putty, the sprayed films showed frequency independent behaviour.

Figure 4:
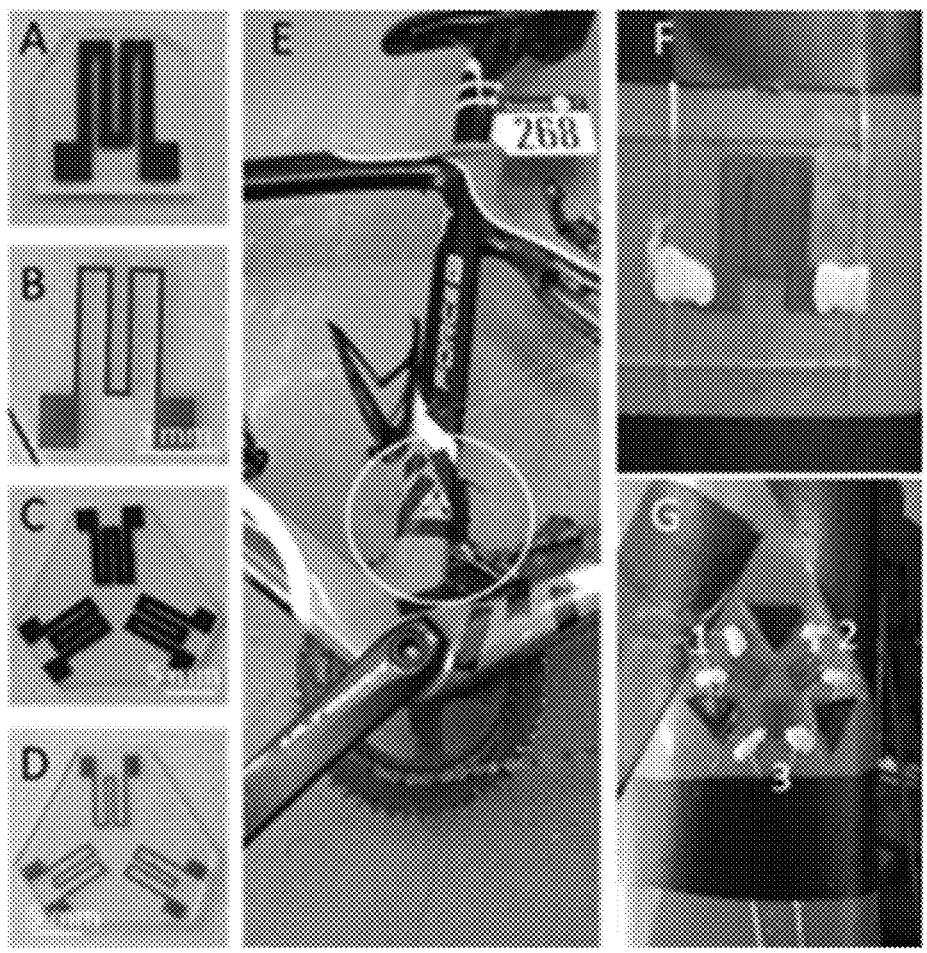
FIG. 4 illustrates an application of printed nanocomposite material of the claimed invention for strain sensing on a bicycle. a-d) Examples of printed strain sensors consisting of single gauges (a-b), printed by (a) screen- and (b) aerosol-jet printing, and rosettes (i.e. triple gauges) (c-d), printed by (c) screen- and (d) aerosol-jet printing. e-f) Photographs showing position the sensor is mounted in the bicycle frame (e) and close-ups showing single gauge (screen printed) and rosette (aerosol jet printed) sensors. h) Resistance-time trace for a screen-printed sensor mounted on a bicycle pedalled at a pedal rotation rate of 0.69 Hz. i) Fourier transform showing the pedalling frequency can be extracted unambiguously. j) Pedalling frequency measured by a G-putty sensor versus actual pedalling frequency (measured using a commercial sensor). The line represents y=x. k) Measured peak-to-peak resistance change (normalised to strain-free-resistance) plotted as a function of peddling power divided by peddling frequency (measured using commercial sensor). Measurements were made for a number of powers, each at three different frequencies. The line shows the scaling expected for a simple oscillator. l) Linear strain in the sensing direction calculated by finite element analysis for the three sensors shown in g as a function of crank angle. m) Resistance as a function of time measured for each of the three sensors making up the rosette in g. The right axis shows the estimated strain calculated using gauge factor=35.
Figure 4:
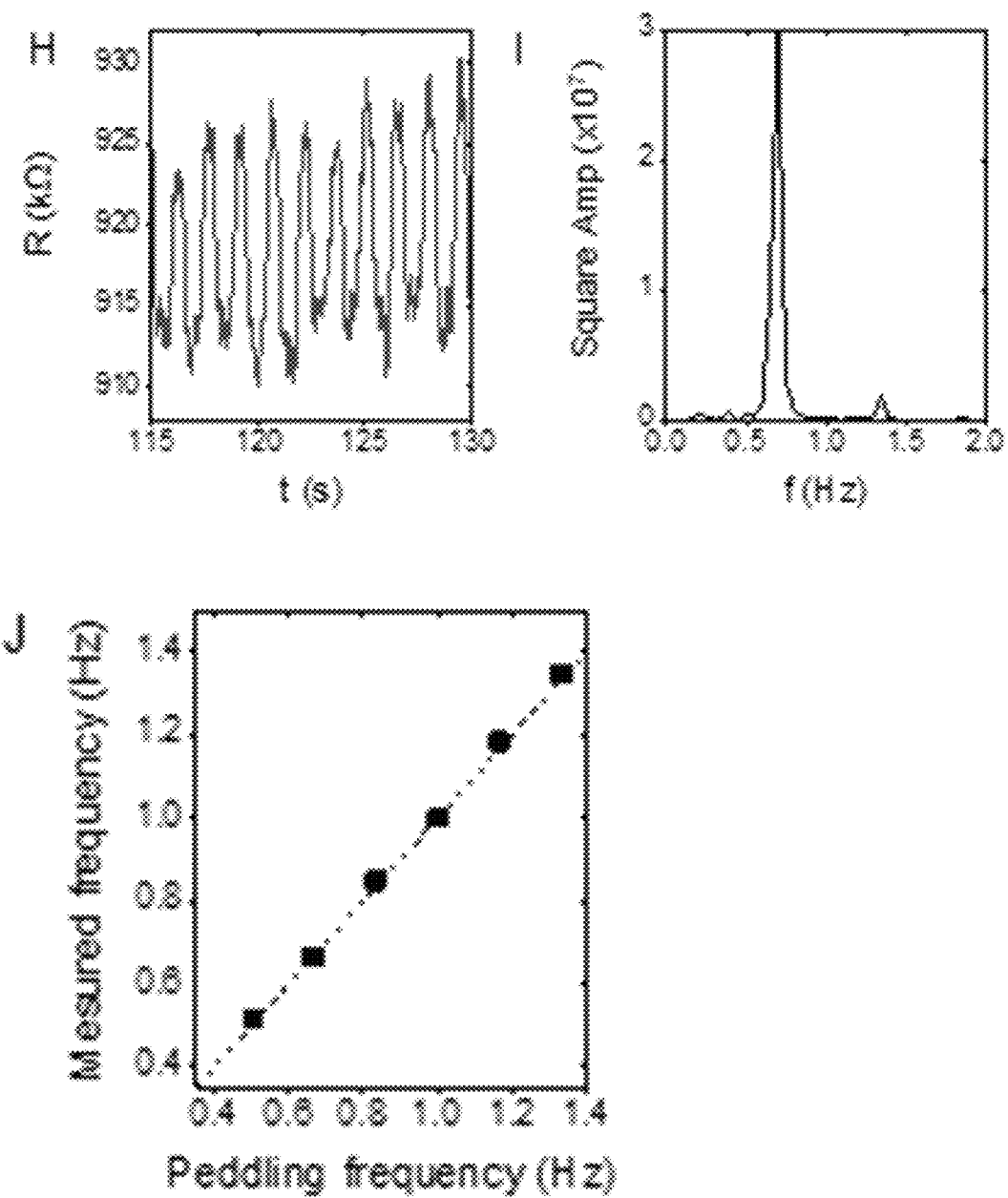
Figure 4:
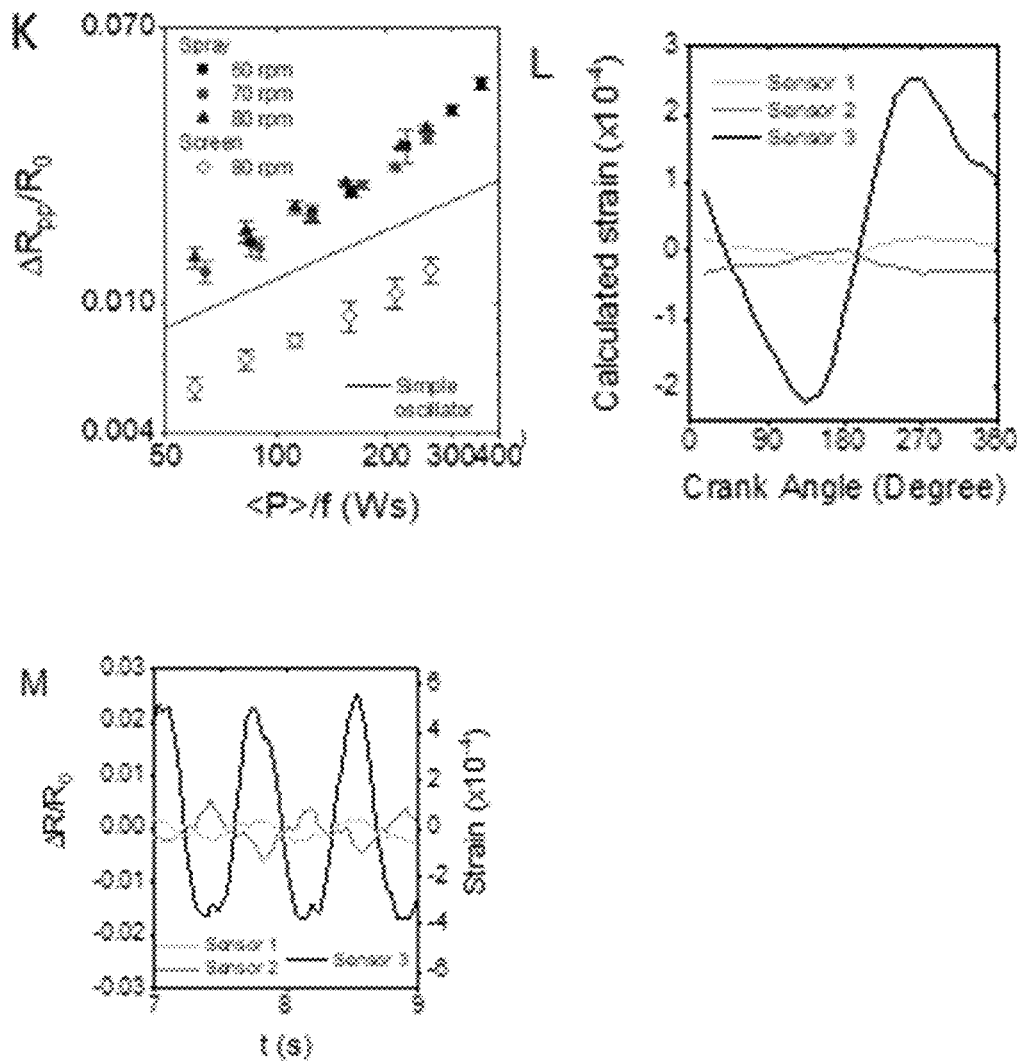

This combination of high conductivity, reasonably large gauge factor and rate- and frequency-independence makes G-putty ideal for strain sensing while its printability allows deposition on a range of substrates and makes patterning straightforward. Strain sensors are generally fabricated in a zigzag-type pattern to maximise sensor length (to increase the resistance change) while minimising the sensor area (to spatially localise the response). Shown in FIGS. 4a-b are examples of such sensors printed onto extremely thin PDMS substrates by screen- and aerosol-jet-printing respectively. It was noted that aerosol-jet printing allows finer features while screen-printing gives greater scalability. In addition, FIGS. 4c-d shows printed combinations of three sensors, each at 120° to each other. Such structures are known as rosettes and can be used to measure strain fields. To demonstrate their use, a novel application was chosen: strain sensing on bicycles.

Power meters in recent decades have become increasing present in the sport of road cycling. They allow a cyclist to quantify pedalling effort by measuring the power output of the pedalling cyclist—a metric that combines both the force applied to the pedals as well as the frequency of the applied pedalling load. Having a means of determining power output enables the cyclist to effectively pace efforts in a precise way that was not possible before. This knowledge is crucial for training effectively and in gauging efforts during races. They also allow a cyclist to quantify improvements in fitness and ability, as their functional power output of a pedalling cyclist rises of the course of training. What makes the act of measuring the power output of a pedalling cyclist possible is the ability to first measure the loading applied at the pedals of the bike.

During use, the frame of a bicycle will deform notably as a result of the forces imparted to it by the cyclist. This deformation can typically be broken down into two categories: vertical deformation and lateral deformation.

Vertical deformation can be the compression and rarefaction of the frame as a result of the loads applied to the frame of the bicycle—an example of this would be the loads transferred though the saddle and handlebars of the bike by the rider. Bike frame manufactures will typically want to maximise vertical deformation as if the frame is compliant in this manner, the frame will absorb the applied loads thereby acting as a kind of shock absorber, leading to a more comfortable riding experience.

Lateral deformation can be the bending and flexing of the frame in the direction perpendicular to the bicycle. The main forces responsible for this kind of deformation result for the loads applied to the pedals of the bicycle by the user. Unlike vertical deformation, bike manufactures aim to limit the amount of lateral deformation present in the frame during use as it means that instead of the power being transferred through the pedals and into the drive train, it is being absorbed by the frame leading to a reduction in cyclist performance. However, due to the thin frontal area of a modern bike frames, lateral deformation is difficult to minimize and is present in all bike frames to a greater or lesser extent depending on the material of the frame used by the manufacture.

The inventors employed printed strain sensors of the claimed invention to this end, utilising the fact that peddling results in small but well-defined oscillatory strains in the bike frame. Using finite element analysis, the inventors identified positions on the frame where these strains were maximised (FIG. 4e, circled) and one which has not been previously reported in literature. In this location on the frame, the axial strain cycles between tension and compression with the same frequency as the loading being applied to the pedals. This allows the user to gather data on two key elements of the cyclist's performance: (i) the power outputted by the cyclist and (ii) the cyclist's cadence. Printed sensors such as that in FIG. 4f were then mounted by sticking the PDMS substrate to the frame. The resistance output of such a sensor is shown in FIG. 4h and demonstrates clear oscillatory behaviour. The Fourier transform of such a trace shows the main frequency to be dominant. It was found that the peddling frequency measured in this way matched extremely well with that measured using conventional devices (horizontal axis). The amplitude of the resistance trace, $\Delta R_{pp}$, is proportional to the strain amplitude, $\varepsilon_0$, and so allows measurement of the power output. For any oscillator vibrating at frequency, f, the mean power inputted is just the average product of force and velocity. In damped, driven oscillators, the force amplitude is proportional to displacement amplitude (i.e. strain amplitude) while we associate the velocity with the strain rate, $\dot{\varepsilon} \propto f\varepsilon$. This yields $\langle P \rangle \propto f\varepsilon_0^2$ and so $\langle P \rangle \propto f[(\Delta R_{pp}/R_0)/G]^2$.

Shown in FIG. 4k is data for the measured resistance amplitude (normalised to $R_0$) plotted versus $\langle P \rangle /f$ for various combinations of peddling frequency and power. The inventors found a well-defined relationship between $\Delta R_{pp}/R_0$ and $\langle P \rangle /f$, reasonably consistent with simple oscillator behaviour allowing resistance measurements to yield power output.

The inventors also demonstrated the use of the rosette to measure the strain field in the bike frame. Finite element analysis was used to estimate the strain due to peddling in the frame along the directions of the sensors marked as 1, 2 and 3 in FIG. 4g. As shown in FIG. 4l, while the axial strain (in direction of sensor 3) is predicted to be dominant, non-zero components should exist in the direction associated with sensors 1 and 2. Shown in FIG. 4M are the measured resistance outputs associated with sensors 1-3 during peddling. While the axial strain (sensor 3) is indeed dominant, oscillatory strains with the correct phases and appropriate magnitudes can be seen in the other two sensors. Using the measured gauge factors of these sensors (G=35), the actual strain on the right axis can be estimated. This shows the maximum strain in sensors 1 and 2 to be $\sim 10^{-4}$ (100 μ-strain), a relatively small value which nicely demonstrates the sensitivity of these printed sensors.

If standard metal foil strain gauges were to be used to measure the axial strain mentioned above, a configuration such as a wheatstone bridge must be used to magnify the poor sensitivity of these strain gauges. As well as this, they must be adhered permanently to the surface of the bike frame by sanding down the surface in conjunction with an adhesive. In most cases, the bike frame is the most expensive component of the road bike, usually coming with a high-quality surface finish. The fitting of permanent metal foil strain gauges is not ideal as the process involved is a high precision task with the possibility of doing structural damage to the frame of the bike. Graphene nanocomposite strain sensors as provided by the claimed invention prove to be an exceptional solution to this problem. When the invention described above is applied to a thin, self-adhesive polymer base, the resulting strain sensor can be applied to the side of the bike frame without any damage to the frame. These sensors are up to more sensitive than standard metal foil strain gauges, which gives the option not to use a wheatstone bridge configuration, making the electronics more compact. In addition to this, the self-adhering nature of the device means that the sensor can be applied to the bike frame in a quick and non-intrusive/non-destructive way. As mentioned above, the cost of manufacturing the sensors is extremely low compared to existing power meters on the market, which typically fall in the range of hundreds of euro and involve permanent alterations to the bike.

Figure 5:
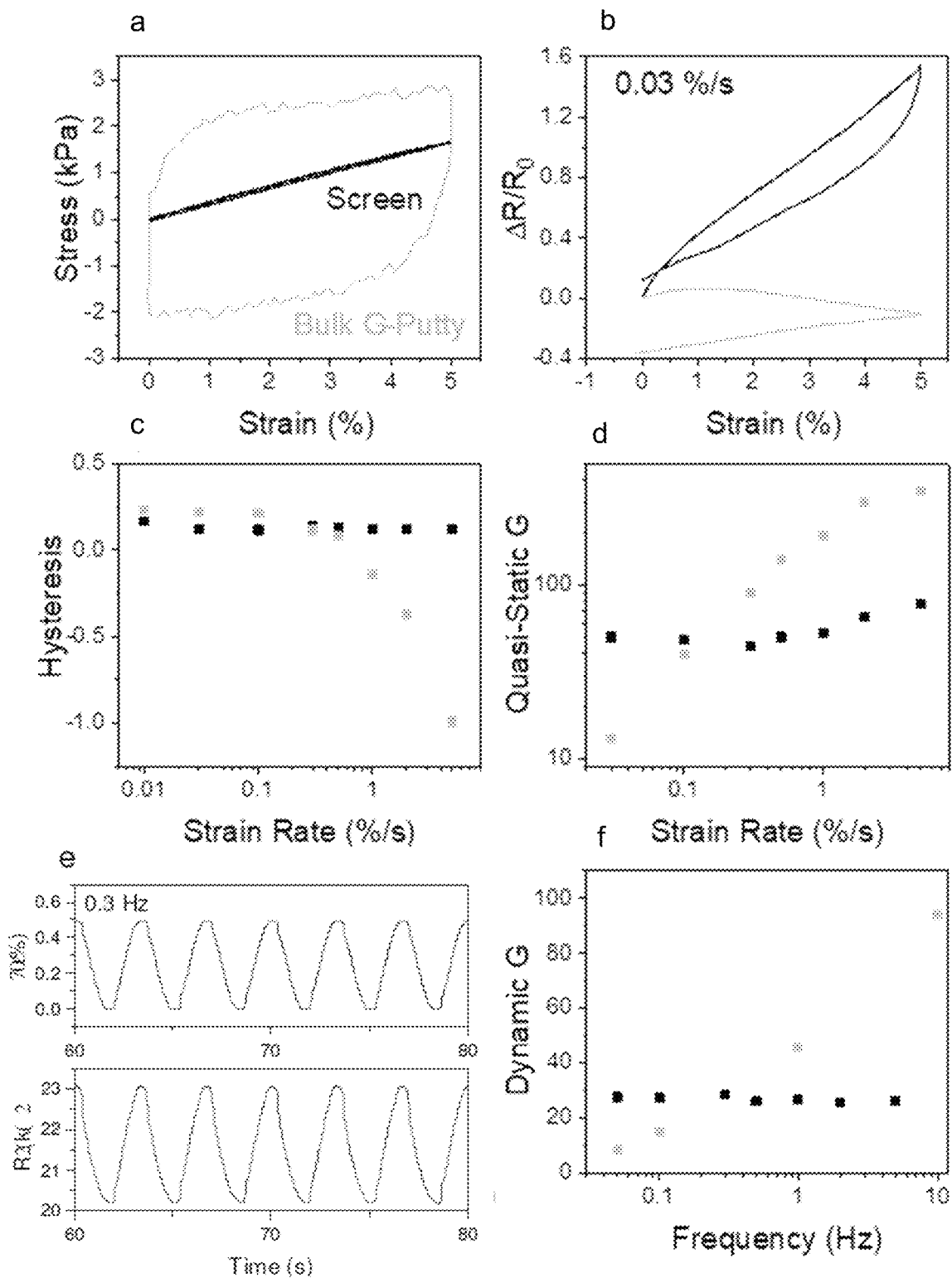
Figure 6:
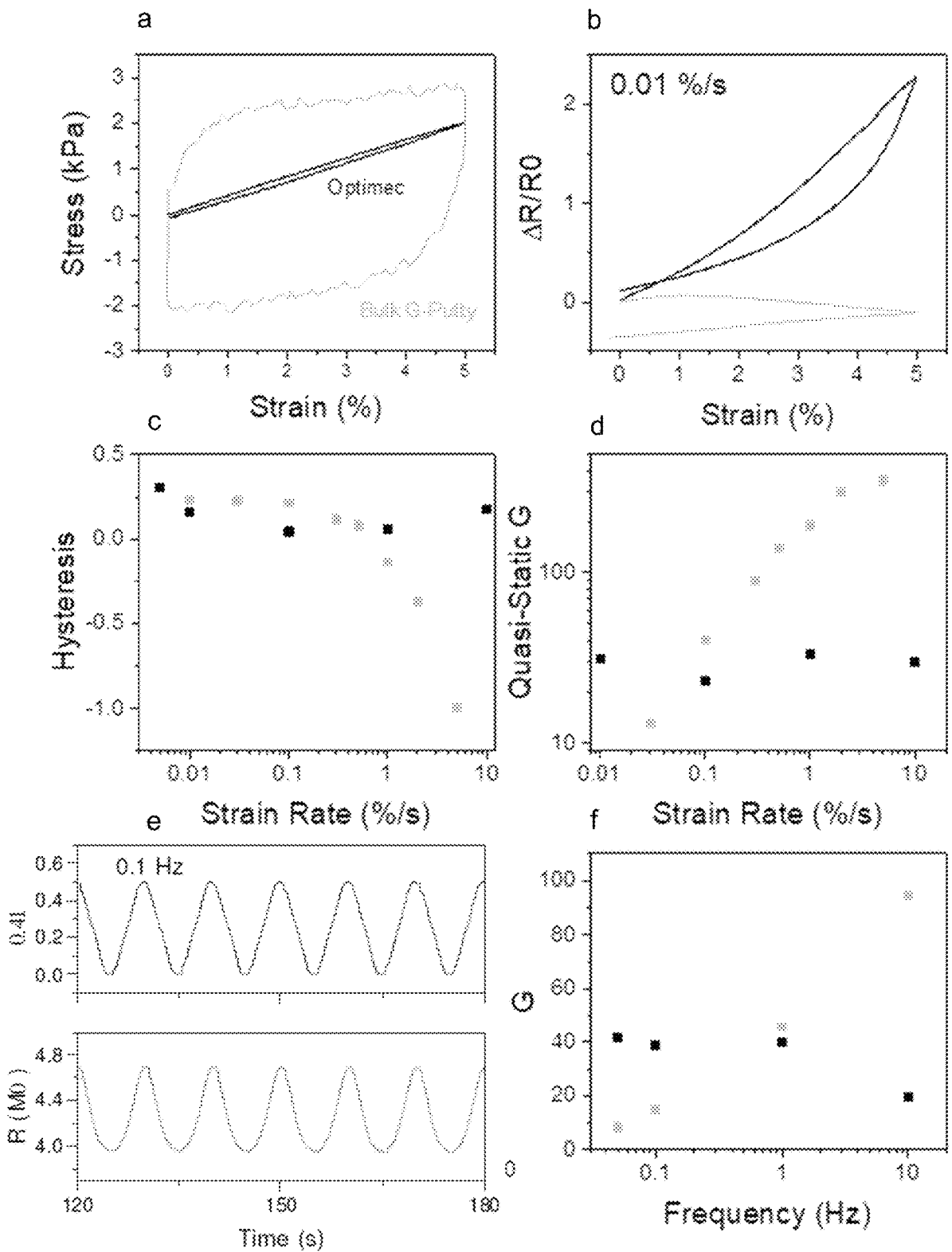

FIG. 5a and FIG. 6a is a comparison of the mechanical hysteresis curves of bulk graphene-polysilicone mixture (G-putty) (grey) to a rectangular sensor of the claimed invention screen printed (FIG. 5a) and optomec printed (FIG. 6a) using the nanocomposite ink onto a PDMS substrate (gold). The mechanical hysteresis of a material is an indication of the energy lost in the material during one mechanical cycle (the material being loaded and unloaded) and can be used to determine the kind of material by looking at the area contained within the loop (viscoelastic, elastic etc.). Viscoelastic materials (for example, G-putty) are not suitable as strain sensors as their properties display a time dependence, i.e., it is necessary to know what part of the cycle the material is in in order to obtain the correct value of the physical property being measured. Elastic materials (printed sensors) display a much smaller area contained within the loop, giving a greater accuracy in measuring the mechanical characteristics of the material as which part of the cycle the material is in is less relevant.

FIG. 5b and FIG. 6b compare the electrical hysteresis (how the fractional change in resistance changes with strain over one mechanical cycle) curves of bulk G-putty (grey) to a rectangular sensor of the claimed invention screen (FIG. 5b) and optomec (FIG. 6b) printed using the nanocomposite ink onto a PDMS substrate (blue and gold, respectively). Again, this demonstrates why bulk G-putty is unsuitable for commercial strain sensing applications. In G-putty, the graphene flakes are mobile within the polymer matrix and long relaxation times are required for the flakes to settle to their optimum configuration for sensing—the longer the material is allowed relax, the better the sensitivity. This flake mobility can be observed as an electrical hysteresis curve with a large difference between the initial and final resistance. This demonstrates the time dependence of the electromechanical properties of this material and highlights the problems for commercial sensing applications. Successive measurements are always taken from a difference in base line resistance which results in a different sensitivity. In the case of the screen and optomec printed sensors of the claimed invention, while there is still a degree of hysteresis present, the final resistance observed is much closer to the starting resistance compared to bulk G-putty. This means that successive measurements will be taken from close to the same value of resistance leading to measurements which are more accurate and reproducible.

FIG. 5c and FIG. 6c is a comparison of the area contained within the hysteresis curve for the bulk G-putty and the screen and optomec printed sensors of the claimed invention, respectively, as a function of the strain rate during the mechanical tests. From this, the hysteresis for the screen and optomec printed sensors of the claimed invention each remain relatively constant (strain rate independent) over the range of strain rates tested, while the bulk G-putty shows considerable variation (strain rate dependent). This all speaks to the accuracy and reproducibility of measurements taken using both kinds of sensors and highlights the problems present in G-putty which have been overcome with printing.

FIG. 5d and FIG. 6d is a comparison between the values of the gauge factor obtained for the bulk G-putty and the screen and optomec printed sensors of the claimed invention, respectively, as a function of the strain rate during testing. Again, the screen and optomec printed sensors of the claimed invention each show a relatively constant, strain rate independent G over the range of strain rates tests. This is in comparison to the gauge factor values obtained for bulk G-putty which shows the material having a strong rate dependence in terms of its sensitivity. This is one of the more significant issue of G-putty as a sensing material as the vast majority of applications involve varying rates of strain.

FIG. 5e and FIG. 6e show the electrical response to a repeating sinusoidal strain of the screen and optomec printed sensors of the claimed invention, respectively. The top panel show how the material is strained with time with the bottom panel showing the electromechanical response of the material. The response is in phase and consistent in amplitude during the testing.

FIG. 5f and FIG. 6f are a comparison between the values of the gauge factor obtained for bulk G-putty and the screen and optomec printed sensors of the claimed invention, respectively, as a function of the frequency that the material was cycled at. Like the rate dependence measurements, the G-putty displays a sensitivity that is dependent on the frequency at which the material is cycled at. This is not the case for the screen and optomec printed sensors of the claimed invention, which show a relatively constant value for G irrespective of the cycling frequency.

In conclusion, the inventors have shown that a G-putty based inks can be printed into patterned thin films with high values of both gauge factor and conductivity. The low film thickness combined with pinning at the film-substrate interface prevents relaxation under strain and supresses electromechanical hysteresis resulting in a sensing response which is independent of both strain-rate and frequency. Printed G-putty-based rosette-type sensors can measure strain fields and strains as low as $\sim 10^{-4}$.

When being used as a wearable sensor in the shoes of a wearer, the nanocomposite material of the claimed invention is printed onto the surface (either upper or lower) of an insole for a shoe, wherein the insole is flexible (or inflexible) and encapsulated in a polymer. The printed nanocomposite material of the claimed invention when printed, is connected to a microcontroller or microprocessor with its own power supply and is adapted to communicate with an app via BLUETOOTH® or other suitable means to relate sensing metrics to a device. From the response of the sensors to the steps taken by the wearer, one can determine the magnitude and distribution of force across the insole and the time frames over which these occur with each foot strike. The metrics relayed by the printed sensors composed of the nanocomposite material described herein include, but are not limited to, force distribution, power, cadence, distance, time, pace, splits, elevation, calories, cadence, step length, foot strike and pronation.

When discussing strain sensors in terms of sensitivity, a metric called the "gauge factor", which looks at the relative change in electrical resistance of the material during straining, is used. Metal foil strain gauges typically have a gauge factor around 2 which is comparatively low compared to other devices. This means that for high precision measurements with low strain amplitudes, it would be difficult to obtain an accurate value using a metal foil strain gauge. The printable nanocomposite of the claimed invention can be made up to 50× more sensitive than traditional foil strain gauges, making them suitable for a range of high sensitivity applications which traditional metal foil strain gauges would not be able to perform in.

Whereas traditional metal foil strain gauges have a set gauge factor, by controlling a variety of different parameters during the manufacturing process of the nanocomposite of the claimed invention, the inventors could tailor the gauge factor of their sensors to between 5 and 120. This ability to tune the sensitivity of the printable nanocomposite material allows for the creation of application-specific sensing devices.

The geometry of traditional strain gauges only allows for strain to be measured in the direction parallel to the windings, making it a fixed direction sensor, i.e., it is only possible to measure strain in a specific direction (unidirectional). This can be overcome with more exotic arrangements but represents a considerable problem in measuring systems where the strains in the material are multidirectional. This can be overcome with more exotic arrangements of sensors but increases the number of strain gauges required in addition to the external circuitry necessary to ensure an accurate signal is obtained. The invention discussed herein is not dependent on a specific geometry in order to perform sensing measurements and can be used to create a truly multidirectional strain sensor. Patterned designs can be printed using the nanocomposite material of the claimed invention but are not a requirement for producing a high-end sensing device. This removes a considerable hurdle in large scale manufacturing.

The resolution of traditional metal foil gauges, the area over which they can detect strain, is limited by the dimensions of the metal foil pattern. The nanocomposite material of the claimed invention is not limited in this regard as it is possible to obtain a device with high sensitivity without the need for a patterned design.

In addition to this, the insulating substrate that the metal is patterned on top is normally quite stiff, typically being made from polyimide, which has a Young's modulus of around 3.5 GPa. This makes high strain measurements difficult to obtain. The nanocomposite material of the claimed invention can be deposited on a variety of substrates making it more suitable for a range of high strain applications.

Current nanocomposite strain sensors are an alternative to traditional metal foil strain gauges and can obtain high gauge factors outside the range of industry standard sensors. However, nanocomposite typically display a large resistance hysteresis meaning that the sensitivity of the sensor is strongly rate dependent. This makes many modern nanocomposite strain sensors suitable only to specific applications where the rate of strain is known and is constant. Rate specific applications, which make up the vast majority of strain sensing applications in industry and in the consumer market, require a sensor whose sensitivity is independent of strain rate. The nanocomposite material of the claimed invention demonstrates a high degree of sensitivity consistently across a range of strain rates and cycling frequencies.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A printed nanocomposite sensor comprising a polymer, a cross-linking agent that forms temporal crosslinks between two or more polymer chains, and a conductive nanomaterial combined to form a nanocomposite material, wherein the nanocomposite material is printed in the form of a film or a sheet on at least a part of a surface to form the printed nanocomposite sensor.

2. The printed nanocomposite sensor according to claim 1, wherein the film or sheet of printed nanocomposite material has a thickness of between about 5 nm to about 500 µm.

3. The printed nanocomposite sensor according to claim 1, wherein the conductive nanomaterial is selected from the group comprising graphene, reduced graphene oxide, metallic nano-particles (MNPs), metallic nano-platelets, metallic nanowires (MNWs), carbon fibres, carbon black, carbon nanotubes (CNTs), and multi-walled carbon nanotubes (MWCNTs).

4. The printed nanocomposite sensor according to claim 1 wherein the polymer is an elastomer selected from the group comprising polybutadiene, butadiene and acrylonitrile copolymers (NBR), natural and synthetic rubber, polyesteramide, chloropene rubbers, poly(styrene-b-butadiene) copolymers, polysiloxanes, polyisoprene, polyurethane, polychloroprene, chlorinated polyethylene, polyester/ether urethane, polyurethane, polyethylene propylene, chlorosulphanated polyethylene, polyalkylene oxide, flurosilicone, highly saturated nitrile (HSN, HNBR), nitrile, polyacrylate, silicone, fluorinated ethylene propylene (FEP), a perfluoroelastomer, a fluroelastomer, a copolymer of tetrafluoroethylene/propylene, carboxylated nitrile, a dipolymer of hexafluoropropylene and vinylidene fluoride, and mixtures thereof.

5. The printed nanocomposite sensor according to claim 1, wherein the cross-linking agent that forms temporal crosslinks between two or more polymer chains is a weak crosslinking agent.

6. The printed nanocomposite sensor according to claim 1, wherein the crosslinking agent that forms temporal crosslinks between two or more polymer chains is boric acid.

7. The printed nanocomposite sensor according to claim 1, wherein polymer is polydimethylsiloxane, the cross-linking agent that forms temporal crosslinks between two or more polymer chains is boric acid, and the conductive nanomaterial is graphene.

8. The printed nanocomposite sensor according to claim 1, wherein the concentration of the conductive nanomaterial in the printed nanocomposite material is between about 0.01 vol. % to about 99 vol. %.

9. The printed nanocomposite sensor according to claim 1, wherein the printed nanocomposite sensor has a gauge factor of between 0.5 and 500.

10. The printed nanocomposite sensor according to claim 1, wherein the sheet or film is encapsulated in a polymer, a thermoplastic, an elastomer, a copolymer, or a combination thereof.

11. The printed nanocomposite sensor of claim 1, wherein the surface is glass, semi-conductors, metal, ceramic, aluminium foil, copper foil, or other stable conductive foils or layers.

12. The printed nanocomposite sensor of claim 1, wherein the surface further comprises an adhesive on the opposite side on which the printed nanocomposite material is on.

13. A method of measuring power output of a cyclist, the method comprising
measuring a strain, using one or more printed nanocomposite sensors of claim 1, exerted by a cyclist on a bicycle frame, wherein the one or more printed sensors are on the bicycle frame.

14. The method of claim 13, wherein the strain exerted on the bicycle frame is measured in a uni-directional or a multi-directional manner.

15. A method of measuring a force generated by a user engaged in running or walking, the method comprising the steps of:
measuring a force applied by a user's foot to one or more of the printed nanocomposite sensor of claim 1 present inside a shoe worn by the user.

16. The method of claim 15 further comprising processing said force data to determine a metric of interest.

17. The printed nanocomposite sensor according to claim 1, wherein the sensor is a strain sensor.

* * * * *